United States Patent [19]
Shadduck

[11] Patent Number: 6,099,521
[45] Date of Patent: Aug. 8, 2000

[54] SEMICONDUCTOR CONTACT LENS COOLING SYSTEM AND TECHNIQUE FOR LIGHT-MEDIATED EYE THERAPIES

[76] Inventor: John H. Shadduck, 1490 Vistazo West St., Tiburon, Calif. 94920

[21] Appl. No.: 09/110,065

[22] Filed: Jul. 3, 1998

Related U.S. Application Data

[63] Continuation-in-part of application No. 09/084,550, May 26, 1998.

[51] Int. Cl.[7] .................................................. A61B 3/00
[52] U.S. Cl. ............................................................ 606/4
[58] Field of Search ..................... 606/4, 5, 6; 351/212, 351/219, 246

[56] References Cited

U.S. PATENT DOCUMENTS

| | | | |
|---|---|---|---|
| 5,616,139 | 4/1997 | Okamoto | 606/4 |
| 5,807,380 | 9/1998 | Dishler | 606/4 |
| 5,820,624 | 10/1998 | Yavitz | 606/4 |

Primary Examiner—George Manuel

[57] ABSTRACT

An active form of heat sink contact lens device that utilizes a series of semiconductor Peltier paired elements operatively connected to a direct current power controller and power source for (i) pre-cooling the cornea before an optothermal treatment of the cornea, (ii) to cool the cornea rapidly following an optothermal treatment of the cornea, or (iii) to dynamically cool the anterior surface of the cornea during an optothermal treatment of the cornea based on temperature feedback from temperature sensors in the contact lens device. The sphero-concave lens with a medial portion of thermally conductive transparent material to allow the transmission of light beams which is formed to contact a patient's cornea. The perimeter portion of the lens also spheroconcave with a radius of curvature adapted to contact the sclera. In general, the semiconductor paired Peltier elements are carried in the perimeter portion of the contact lens device.

3 Claims, 27 Drawing Sheets

SEMICONDUCTOR CONTACT LENS COOLING SYSTEM AND TECHNIQUE FOR LIGHT-MEDIATED EYE THERAPIES

CROSS-REFERENCE TO RELATED APPLICATIONS

This application is a Continuation-In-Part of the following co-pending and commonly invented U.S. patent application Ser. No. 09/084,550 (Atty. Docket No. S-15-005) filed May 26, 1998 titled "Apparatus and Technique for Light-Mediated Strain Relaxation in Corneal Topographic, Refractive or Orthokeratologic Procedures" incorporated herein by this reference. This application also is related to co-pending U.S. patent application Ser. No. 09/102,533 (Atty. Docket No. S-DESC-003) filed Jun. 22, 1998 titled "Devices and Techniques for Light-Mediated Stimulation of Trabecular Meshwork in Glaucoma Therapy," the complete disclosure of which is incorporated herein by this reference.

BACKGROUND OF THE INVENTION

1. Field of the Invention

The present invention relates to an apparatus and technique for thermal treatment of a patient's cornea to facilitate correction of refractive disorders, and more particularly, to an apparatus and technique that may be used in conjunction with corneal diagnostic procedures to obtain strain-relaxed corneal topographic information for improving outcomes of follow-on refractive treatments (i.e., orthokeratology or laser treatments such as laser keratectomy and laser keratomilieusis).

2. Description of the Related Art

In recent years, computerized corneal topography systems have been refined to provide better information on which ophthalmic surgeons can base various refractive corrections and surgeries. Corneal topography measures the anterior surface of the cornea, typically by using concentric rings of light projected onto the anterior corneal air/tear interface to create a virtual image and yield data that may be registered relative to a fixed plane with a high resolution camera. A topographic program (algorithm) converts such data points into radii of curvature by measuring the spatial position of each ring on the previously uncharted elliptical curve of the cornea along any meridian. The algorithms are adapted to produce 2-dimensional or 3-dimensional color maps of the anterior and/or posterior surfaces of the cornea. FIG. 1A shows a patient's eye 5 with iris 2 and sclera 7. The curvature of the anterior surface of cornea 6 in FIG. 1A is represented in FIG. 1B as a color-coded topographic map with asymmetric islands indicating an irregular astigmatic non-spherical shape. FIG. 2A shows eye 5 again with FIG. 2B representing the curvature of the posterior surface the cornea 6, again with an irregular curvature. FIG. 3 shows a cross-sectional or pachymetry map (thickness) of cornea 6 along a meridian which shows that the cornea has an irregular thin section indicated at A. Such pachymetry data can be derived by topographic algorithms from the anterior and posterior surface data. The corneal topographic information as shown in FIGS. 1B, 2B and 3 allows refractive surgeons to more effectively execute corrective surgical strategies. In general, the ophthalmic surgeon's objective is be alter the shape of the anterior surface of the cornea to be more spherical, e.g., either to have a flatter curvature to correct myopia or to have a steeper curvature to correct hyperopia.

As background, refractive disorders of the eye result from the inability of the eye's optic system, consisting of the dome-shaped cornea and the crystalline lens just behind it, to properly focus images on the retina, the nerve layer at the back of the eye. Approximately 80 percent of the refracting power of a human eye is within the cornea. When the cornea is mis-shaped, or the eye is too long or too short along its optical axis, or when the lens of the eye does not function normally, a refractive error occurs. Refractive errors generally include myopia, hyperopia, presbyopia and astigmatisms. Myopia is a refractive error that causes poor distance vision, and is characterized by an elongate eye or steepened corneal shape. This condition causes distant images to focus in front of the retina rather than directly on it. Hyperopia is the opposite, and is caused by a shortened eye or flattened cornea that focuses images beyond the retina. Presbyopia results from aging and is a form of farsightedness caused by diminished ability of the lens to elastically change to refract light. Astigmatism is a condition which causes blurred vision for both near and far objects. In an astigmatic patient, the cornea may be shaped like the back of a spoon rather than having a spherical shape (see FIG. 1B). Such an asymmetric corneal shape creates different retinal focal points. Hence, instead of images focusing on the retina, the images focus on a number of points around the retina resulting in a blurred image.

The optimal shape for a cornea is that of a perfect sphere assuming that axis of the eye is normal relative to the other eye. Glasses and contact lenses correct refractive errors by refracting (bending) light before it reaches the cornea and is transmitted through the lens, in other words, changing the angle at which light enters the cornea.

Several types of surgical procedures have been developed to correct refractive disorders such as myopia, astigmatisms and hyperopia by changing the shape of the cornea. For example, laser procedures can reshape the patient's cornea to some extent to a corrected more spherical shape, the most common procedures being laser in-situ keratomileusis (LASIK) and laser photorefractive keratectomy (PRK). LASIK and PRK correct vision by recontouring the anterior layers of the cornea by means of surface ablation with a laser. Orthokeratology is the practice of a different strategy for correcting refractive disorders wherein the affected eye is fitted with a series of progressively different shaped contact lens in order to mold the shape of the cornea, with a retainer contact lens adapted to maintain a final desired shape.

It is useful to provide a description of the anatomy of the patient's eye. FIG. 4A depicts patient's eye 5 which comprises a system of cornea 6 and lens 3 which focuses light on the retina indicated at 4 which is at the back of the substantially spherical body defined by sclera 7. The anterior chamber 8 (and aqueous humor 9a therein) is separated from the vitreous body 9b by lens 3. Thus, cornea 6 forms the anterior wall of chamber 8 and also acts as a lens element. The cornea 6 is a smoothly curved transparent structure which has a smaller radius of curvature than the opaque sclera 7 and bulges from the smooth outer spherical surface of the eye. Refractive errors occur when the lens elements do not focus incoming light on retina 4.

The cornea 6 is uniquely structured to transmit light into the eye. The primary structure of the cornea is the stroma, which comprises approximately 90–95 percent of the cornea's thickness. As can be seen in FIG. 4B, the stroma is comprised of lamellae L which lie in flat sheets and extend from limbus to limbus 11. Each lamella (layer or sheet) consists of strong, uniform, parallel collagen fibrils which are maintained in a regularly spaced hexagonal separation by a ground substance or GAGs (for glycoaminoglucans, also called a glycoprotein and mucopolysaccharide matrix). Between the lamellae are keratocytes layers KL (the fibroblasts), the constitutive cells of the cornea which produce the GAGs and support synthesis of collagen. The substantial thinness of the collagen fibrils together with the regularity and dimensions of the intrafibril spaces allow the cornea to be substantially transparent (along with the fact that the cornea is avascular). The exquisite spacing of the collagen fibrils—and thus transparency—is maintained osmotic pump mechanisms that dehydrate the cornea.

A normal cornea maintains about 75 to 80 percent water (by weight) in a unique equilibrium condition wherein the cornea structure is substantially dehydrated relative to surrounding tissue volumes. In other words, the corneal structure with collagen-containing lamellae L and keratocyte layers KL is constantly under significant compressive forces by what may be termed as an osmotic "pump" or dehydration mechanism. For example, if the outer epithelial layer or inner endothelial layer of cornea 6 is extensively destroyed or removed, within 24 hours the thickness of the cornea will increase from 200 to 500 percent, since the absence of corneal integrity prevents the dehydration mechanisms from pumping fluid from the cornea quickly enough. Several factors are considered critical in maintaining the relative dehydration of the cornea besides epithelial and endothelial integrity: (i) osmotic and electrolytic equilibrium, (ii) metabolic activities in the stroma, (iii) evaporation of water through the anterior corneal surface, and (iv) intraocular pressures. For the purposes of this disclosure, it can be stated that electrolyte and osmotic balances are the most important factors in corneal dehydration. In simplistic terms, the cornea is a composite of connective tissue (collagen fibrils in lamellae) and GAGs limited anteriorly and posteriorly by cellular sheets (epithelium and endothelium). It is believed that both the epithelial and endothelial cells "pump" $Na^+$ and $Cl^-$ ions inward into the stoma and outward into both the tear film and the aqueous humor 9a to help dehydrate the stoma. The osmotic pressure of the stromal fluids probably cause an even more significant regulatory force in moving fluids out of the cornea. The tear film and aqueous humor are believed to be hypertonic to stromal fluids and thus can play an active role in corneal dehydration by constant removal of $H_2O$ through the anterior and posterior corneal surfaces. These osmotic and electrolytic pump-like forces operate on a normal cornea to maintain the stroma in a relative state of dehydration.

The morphology of the cornea is determined largely by the interaction of the above-described fluid flow or "pump" forces as constrained by the tensile strength of the collagen fibrils in the lamellae L. All these forces vary relative to one another and are transient resulting in an equilibrium. The resulting corneal dehydration causes significant biomechanical compressive effects, or strain/stress forces, between and amongst the lamellae L and other microstructure of the stroma. It is postulated that such transient intrastromal straining forces render corneal topographic data (under current practice and technology) to be somewhat inaccurate for predicting the effects of follow-on surgery, particularly since all such surgeries affect epithelial integrity and release lamellar strains and stresses with unknowable effects. Preferably, the ophthalmic surgeon would have topography data that would factor in such transient osmotic pump forces and straining forces to provide a more prefect set of topographic data, or strain-relaxed and stabilized topographic data. A principal objective of the present invention is to use a sequence of temperature elevation (and lowering) within the lamellae to cause plastic deformation of the lamellae into such a strain-relaxed geometry, thus allowing measurement of strain-relaxed corneal curvatures and strain-relaxed pachymetry. It is believed that such strain-relaxed data will allow surgeons to improve outcomes in the more-or-less automated refractive laser surgeries now practiced, wherein corneal sculpting is directed and accomplished with reference to pre-op corneal topographic data. Further, it is believed that strain-relaxed data will allow surgeons practicing orthokeratology to improve or speed up the attainment of corneal shape changes with contact lens changes.

SUMMARY OF THE INVENTION

The system of the invention is termed an LMSR device for its method of light-mediated strain/stress relaxation of the stromal lamellar structure within a patient's cornea. The term lamellar structure is defined herein as the collagen-containing lamellae, its GAGs together with interleaved keratocyte layers. The LMSR device is most particularly adapted for use in developing strain-relaxed corneal topographic data. In this respect, the device may be considered and an adjunctive procedure for use with laser refractive procedures such as LASIK (laser in-situ keratomileusis) and PRK (laser photorefractive keratectomy) as will be described herein. The LMSR device may be even more suited to provide corneal strain relaxation in a periodic treatment to facilitate orthokeratologic procedures, wherein the changes in the series of progressively shaped contact lens may be accelerated, both in accelerated differences in lens shapes and in acceleration of the time intervals between lens changes.

The present invention includes several cooperating systems to develop photothermal effects at appropriate spatial locations and depths in stromal lamellae to optimize strain relaxation. Each stromal location that is elevated in temperature as described below will be strain-relaxed to a certain extent. The LMSR device includes (i) spatial application systems to target photonic beams at locations on the anterior surface of the cornea, (ii) photonic energy sources having wavelengths appropriate for absorption below the anterior surface of the cornea, and (iii) dosimetry control systems for controlling the length and power of the photonic beam exposure at particular spatial locations.

The spatial application component of the invention provides a plurality of photonic beam emitters that project beams in a scanned pattern in or about separate quadrants of an annular ring about the visual axis of the patient's cornea. The beams are generated by a suitable source of light, either coherent or non-coherent, which preferably is a CW (continuous wave) diode source. The emitters typically comprise a combination of elements that transmit the photonic energy beam from the source toward the patient's eye (e.g., a laser diode together with optics, mirrors, and scanners). The spatial application system of the invention further includes programs or algorithms capable of directing the plurality of beams to any selected coordinates on the anterior surface of the cornea.

Of particular interest to the invention, the plurality of emitters are angularly spaced in opposition around an optical axis of the device that is aligned with the visual axis of the patient's eye, thus (i) allowing symmetry and simultaneity of multiple beam incidences relative to eye's visual axis which is not possible with a single scanned or moving beam, and further (ii) allowing an adjunct optical or acoustical treatment (diagnostic or therapeutic) to occur concurrently along the unobstructed visual axis. Thus, the LMSR system can be used simultaneously with a corneal topographic diagnostic instrument operating about the eye's visual axis, or any other laser therapy operating about the visual axis.

By means of research with various wavelengths of photonic energy, it has been determined that the preferred wavelength range for light-mediated lamellar strain relaxation lies in the near-infrared portion of the spectrum, preferably in the range of about 1.32 to 1.70 microns ($\mu$m). It is believed that absorption coefficients related to the above range, or a subset of the range of about 1.44 to 1.55 microns, will prove best suited for such lamellar strain relaxation. The depth of such wavelength absorption will extend through most, if not all, of the thickness of the cornea.

For the proposed method of lamellar strain relaxation, the targeted stromal region may be elevated in temperature to a range between about 42°–58° C. for a period of time ranging from about 2 seconds to 120 seconds, or more precisely within a range of about 42° to 54° C. for such a time period. The optimal therapeutic effects will result from a balance of appropriate light energy wavelength, power level and exposure duration, the length of exposure which obviously relates to scanning paths and speeds. The LMSR treatment, it is believed, will have a quantifiable effect on intralamellar strains by the thermal release of osmotic forces and other lamellar strains and microstructural stresses, all without significant damage cell death in the keratocyte layers. The light-mediated lamellar strain relaxation techniques proposed herein differ greatly from other common laser-tissue interactions. The LMSR technique develops only low energy densities in the stroma as can be seen in the chart of FIG. 4C where various temperature levels indicate different effects on tissue. Below about 60° C., there is no tissue contraction, coagulation or tissue denaturation, or collagen shrinkage. The other categories of laser-tissue interaction include (i) the photodisruption or vaporization modality, wherein photons of the laser beam explosively disrupt the chemical bonds of molecules to vaporize tissue, and (ii) the photocoagulation modality wherein photons elevate tissue temperatures sufficiently to coagulate, denature, shrink or desiccate tissues. In the present invention, the objective is not photodisruption or photocoagulation, but the use of much less energetic photons in the wavelength domain of about 1.32–1.70 microns which is herein termed a photoresonance modality which causes atoms to resonate rapidly thus increasing temperatures without disrupting any intramolecular chemical bonds.

The dosimetry control component of the LMSR device can be adapted to control timing and power levels of energy delivery in various operational modes. A basic mode of operation can follow a pre-set program of timing and power based on treatment experience. Other operational modes can be based on a feedback-control system based on signals from a radiometric monitor, such as liquid $N_2$ cooled HgCdTe infrared (IR) detector. Such dosimetry control system is adapted to operate with the computer controlled spatial application system.

In general, the present invention advantageously provides a device having an arrangement of a plurality of N spatial beam applicators or scanners positioned about a central axis the device and a patient's eye to allows such axis to be free for concurrent adjunctive light energy treatments, either diagnostic or therapeutic.

The invention advantageously provides a device having an arrangement of N off-axis spatial beam applicators that allows N applicator to strike N quadrants of the cornea each at an incidence of about 90° degrees to such quadrant to minimize reflection of photonic energy.

The invention advantageously provides a device having N spatial beam applicators that allows opposing applicators to direct photonic energy beams at opposing quadrants of the cornea simultaneously to provide a substantial symmetry of treatment.

The invention further advantageously provides a device having N spatial beam applicators that allows each if the N applicators to direct photonic energy beams at independent power levels and in independent patterns in opposing quadrants of the cornea simultaneously to provide a refined method of energy delivery.

The invention advantageously provides a device having a system of delivering photonic energy beams at a cornea to cause relaxation of intralamellar corneal strains and stresses to facilitate follow-on refractive strategies.

The invention advantageously provides a device having a system of delivering photonic energy beams at a cornea to cause relaxation of intralamellar corneal strains without causing significant cell death in keratocyte layers in the cornea.

The invention advantageously provides a device having a system of delivering photonic energy beams at a cornea to cause relaxation of intralamellar corneal strains with a CW diode laser source for avoiding high peak temperatures associated with pulsed lasers.

The present invention advantageously provides a device and method having an arrangement of N off-axis spatial beam applicators that allows the applicator to strike N quadrants about the visual axis of the cornea that may be incorporated into an integrated laser energy system performing corneal strain relaxation and a concurrent LASIK or PRK procedure.

The invention advantageously provides a device having an arrangement of N off-axis spatial beam applicators that allows the applicator to strike N quadrants about the visual axis of the cornea that may be incorporated into an integrated laser energy system performing corneal strain relaxation and corneal topography.

The invention provides a device and method capable of delivering multiple wavelengths of photonic energy beams to a patient's cornea to cause relaxation of intralamellar corneal strains at different depths in the cornea.

The invention provides a device capable of delivering wavelengths of photonic energy beams to a patient's cornea to cause relaxation of intralamellar corneal strains without altering the morphology of the cornea or its transparency.

The invention advantageously provides a device and method for delivering photonic energy beams at a patient's cornea together with a heat-sink contact lens for causing relaxation of intralamellar corneal strains and simultaneously lowering the temperature of the anterior surface of the cornea with the heat-sink to protect the corneal epithelium.

The invention provides a device and method for delivering photonic energy beams at a patient's cornea together for causing relaxation of intralamellar corneal strains together with a non-contact infrared sensor to deliver signal to a feedback-controlled dosimetry control system to prevent excessive temperature elevation in the cornea.

Additional features and advantages of the device and method of the present invention will be understood from the following description of the preferred embodiments, which description should be taken in conjunction with the accompanying drawings.

BRIEF DESCRIPTION OF THE DRAWINGS

FIG. 10A being a partial sectional view of a patient's eye in treatment position with an incident beam FIG. 10B is a full-thickness sectional view of the cornea taken along line 10B—10B of FIG. 10A.

FIG. 10C a further enlarged sectional view of a number keratocyte layers and lamellae of the stroma of FIG. 10B.

FIG. 10D being a view of the normal lattice-like arrangement of collagen fibrils in the lamellae of FIG. 10C.

FIG. 10E being a view of a disrupted lattice of collagen fibrils in the lamellae of FIG. 10D FIG. 10F being a greatly enlarged sectional view of the lamellae of FIG. 10C take prior to thermal treatment with a photonic energy beam FIG. 10G being a view similar to FIG. 10E following absorption of photonic energy indicating relaxed intralamellar strains and stresses and intralamellar movement.

DETAILED DESCRIPTION OF THE INVENTION

Figure 5:
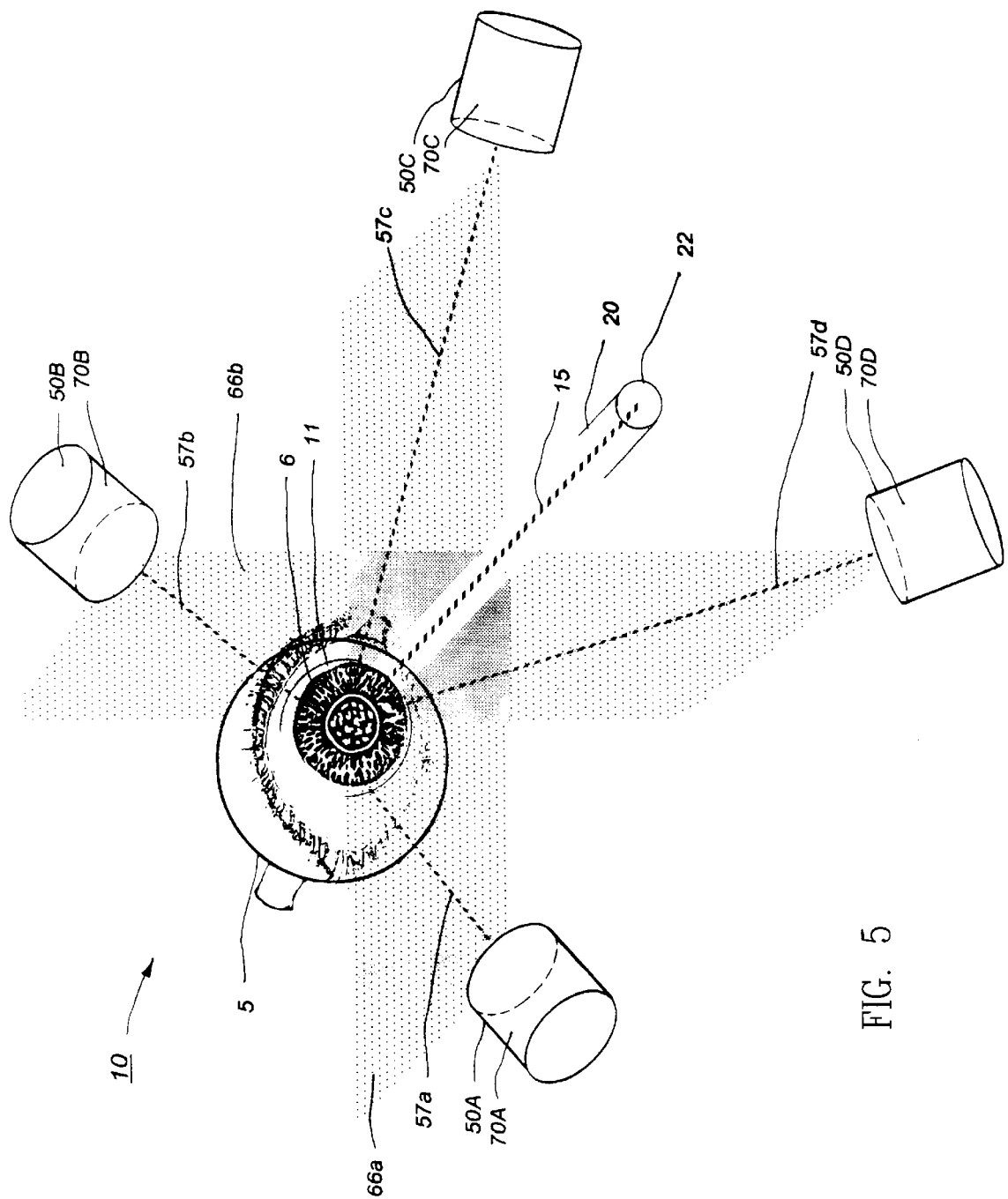
FIG. 5 is an axionometric representation of a light-mediated strain relaxation device of the present invention depicting a plurality of photonic energy emitters in relation to the eye of FIG. 1A.

Referring now to FIG. 5, a schematic view of the present invention or photonic energy delivery device 10 is shown in relationship to a patient's eye 5 which is adapted for a light-mediated (or thermally-mediated) strain/stress relaxation of the corneal lamellar structure. The strain relaxation system is particularly adapted for use in an adjunctive role with corneal topography systems to provide improved diagnostic information relating to anterior and posterior corneal surface curvatures and pachymetry under lesser lamellar strain levels. The invention also may produce useful data by comparing topographic and pachymetric values before and after lamellar strain relaxation. It is believed that such a strain relaxation system will prove important in various topographic diagnostic procedures and allow improved outcomes in follow-on refractive surgical procedures, as well as in orthokeratology programs. The system is herein referred to as a LMSR device (light-mediated strain/stress relaxation). The lamellar strain relaxation device may prove particularly useful in a simultaneous, adjunctive role with laser refractive procedures such as LASIK (laser in-situ keratomileusis) and PRK (laser photorefractive keratectomy) as will be described herein.

The LMSR device 10 of the invention includes systems and mechanisms to provide photothermal effects in appropriate stromal lamellae (depthwise in cornea) for optimal therapeutic results, which desired strain relaxation effects stem from a balanced combination of (i) systems for spatial application or targeting of photonic energy beams at locations or paths on the anterior surface of the cornea, (ii) selection of appropriate wavelength ranges from a photonic energy source for penetration below the anterior surface of the cornea to cause lamellar strain relaxation, and (iii) systems for controlling the length and power of the beam exposure at locations on the anterior surface of cornea, herein termed dosimetry control systems. These systems and aspects of device 10 will be described in order below, and subsequently in their use in performing methods of the invention.

1. Spatial Application Systems for Photonic Energy Beams. FIG. 5 illustrates the spatial application (SA) system for the photonic energy beams of the LMSR device 10. In FIG. 5, it may be assumed that the patient's eye is in a suitable treatment position, by which is meant either (i) that the patient is in an upright position as when his or her chin is on a chin rest of a slit lamp-type device, or (ii) that the patient is in a reclining position (e.g., a LASIK, PRK or other similar procedure).

Figure 6:
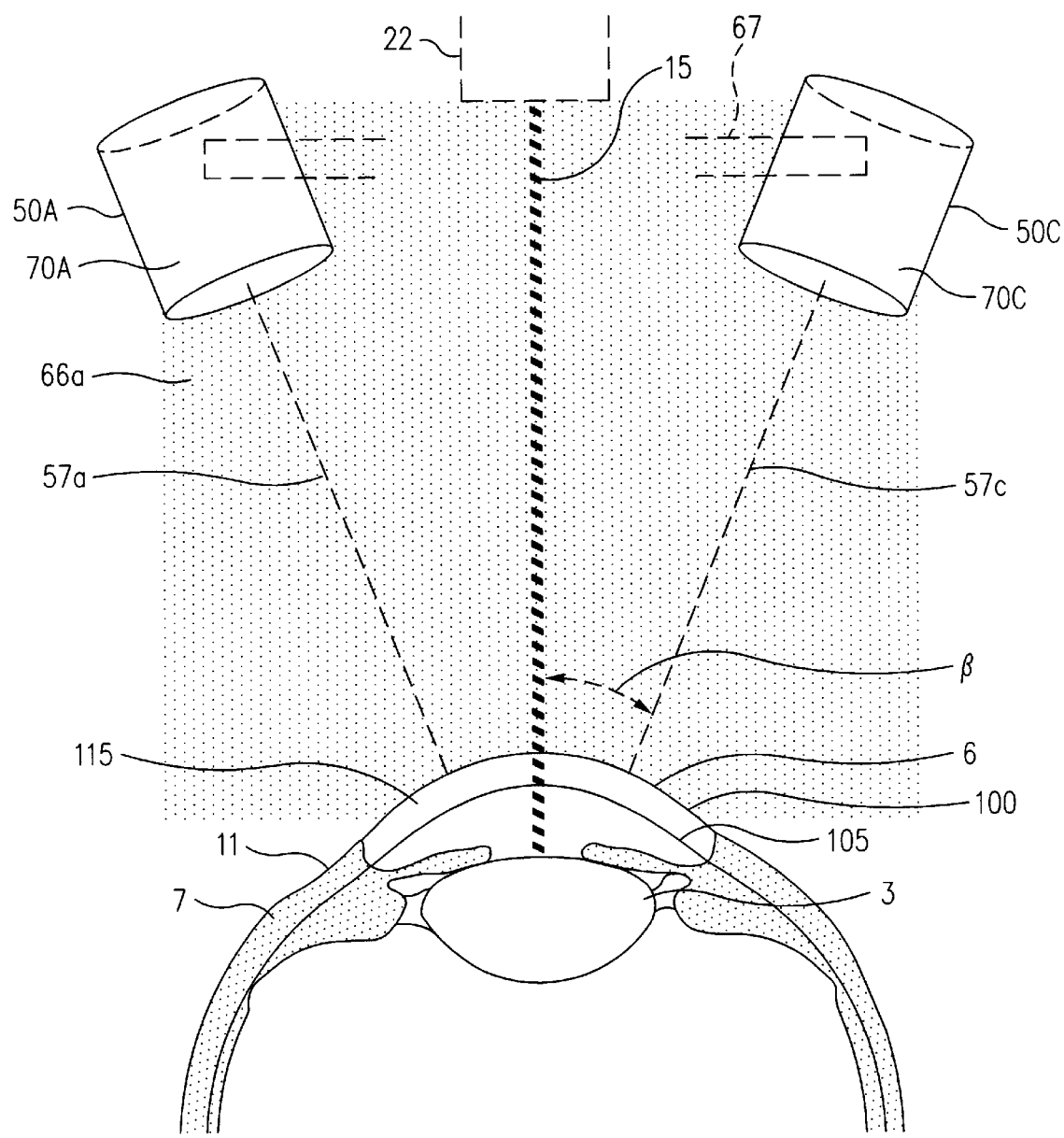
FIG. 6 is a cross-sectional view of the cornea of the eye of FIG. 5 and two of the emitters of FIG. 5.

FIGS. 5–6 shows the patient's eye 5 having optical or visual axis 15, which is herein defined as a central axis of the cornea and lens which directs light onto the retina. A co-axial cylindrical light corridor 20 from about 2 to 20 mm. in diameter is shown around optical axis 15 in FIGS. 5–6, which relates to the path along which light enters the eye as well. More particularly, corridor 20 is free from physical interference from device 10 allowing light beams from other diagnostic apparatus 22 to be used concurrently with device 10 for topographic imaging of the cornea prior to, during and after lamellar strain relaxation. (The LMSR device also can be used concurrently with a treatment device such as LASIK, PRK indicated at 22 or other light-energy or radio-thermal refractive procedure).

In FIG. 5, the LMSR device 10 of the present invention provides a plurality of photonic beam (or light energy) emitters 50A–50D, each of which is indicated as emitting a photonic energy beam (see beams 55A and 55C in FIG. 6) that may be projected generally in a scanned pattern about an axis (57a–57d) shown in FIG. 5 toward a quadrant of eye 5. In FIGS. 5–6, the emitter axes 57a–57d represent a "repose" position of each emitter, where repose is defined as an axis more or less central to the zone around which the spatial applicator can scan. The beams 55A–55D may be provided by any suitable source of light, either coherent or non-coherent, and preferably is a CW diode light source of a type and wavelength described below. It should be appreciated that the term "emitters" is used herein to describe the point or point source at which beams 55A–55D are emitted from device 10 toward eye 5, and as such, the emitters are to be considered as a final element in a possible combination of elements that transmit the photonic energy beam (55A–55D) from a light source or sources 65 (e.g., a laser diode unit, pulsed or pumped laser, or filament-based non-coherent light source) toward the eye. The combination of elements typically includes, but is not limited to the light source(s) 65 together with optics or fiber optics, lenses, mirrors, filters, splitters, combiners, energy attenuators, and scanners (described below) and other arrangements operatively connected to light source 65 to provide the photonic energy beams or radiant emissions 55A–55D from the emitters 50A–50D. It further should be appreciated that the number (N) of emitters 50A–50D may range between two and ten (N=2 to 10) and be angularly spaced in opposition around optical axis 15 of eye (which reference number also indicates an optical axis of LMSR device 10) and fall within the scope of the present invention. Preferably, the number N of emitters ranges from 2 to 4. The plurality of emitters and their symmetrical arrangement in opposition to one another relates to an important aspect of a method of the invention wherein thermal treatment of the stromal lamellae may be simultaneous along (and below the surface of) any meridian at generally opposing sides of the cornea a distance away from the eye's axis 15, thus providing a symmetry and simultaneity of treatment relative to visual axis 15. This manner of treatment is to be contrasted with an asymmetric or non-simultaneous manner of treatment at one side of the cornea and then the other side. The advantages of such symmetric and simultaneous treatment aspects of the invention will be described further below.

Then for convenience, referring to FIG. 5, the emitters 50A–50D in this preferred 4-emitter embodiment of device 10 are spaced at 90° relative to optical axis 15 such that opposing emitters 50A and 50C are generally aligned toward axis 15 within a corneal cross-sectional plane indicated at 66a of FIG. 5. Correspondingly, emitters 50B and 50D are oriented relative to axis 15 along a perpendicular and intersecting cross-sectional plane indicated at 66b.

The LMSR device 10 and each emitter (50A–50D) includes a spatial application (SA) mechanism that is computer controlled for precise physical targeting or application of the photonic beam (55A–55D) that is emitted from each emitter toward the anterior corneal surface. In this preferred embodiment of FIG. 5, it can be seen that each emitter 50A–50D includes such a spatial applicator or scanner comprising an independent x-y galvanometric scanner (or and x-y-z galvanometric scanner) indicated at 70A–70D. Such scanner, for example, may be programmed to operate as a raster scanner, vector scanner or step scanner in order to scan in a particular path or zone as will be described below. An example of such scanner is combination of Model No. M2 or M3 scanners, or series HPM optical scanner available from General Scanning, Inc., Watertown, Mass. 02127.

As can be seen in FIG. 6, emitters 50A–50D are carried in any suitable support frame or structure 67 such that axes 57a–57d along which each emitter 50A–50D emits a photonic beam are angled relative to optical axis 15 at angle β which may range from about 5° to 45°; and preferably in from about 5° to 30°. In other words, referring to FIG. 6, each emitter axis 57a–57d in its repose position is preferably angled approximately perpendicular to the anterior surface of the cornea. The distance of the emitter from the cornea is from about 5 mm. to 300 mm. outward from the anterior corneal surface. Preferably, the axes 57a–57d of the emitters in the repose position are incident upon such anterior surface at a distance outward from the eye's axis 15 ranging from about 1 mm. to 8 mm. As can be seen in FIG. 6, the circle having a radius of R1 indicates a 3 mm. distance from axis 15; the circle with radius R2 indicates a 6 mm. distance from axis 15. FIGS. 5 & 6 show that the positioning of emitters 50A–50D outwardly from the axis of the patient's eye when in a treatment-ready position with such emitters at such a generally perpendicular angle relative to the anterior corneal surface allows any concurrent adjunctive eye treatment such as corneal topography (also, e.g., LASIK or PRK) along the unobstructed optical is 15 and corridor 20. FIG. 5 illustrate that treatment corridor 20 is scaled at approximately 2 mm. to 10 mm. relative to eye 5; FIG. 6 indicates that a corridor 20 may be provided ranging from about 10 mm. to 20 mm. or more in diameter and still not physically interfere with emitters 50A–50D.

Referring again to FIG. 6, supporting frame 67 is shown carrying the emitter array (emitters 50A–50D) in a fixed spaced-apart relationship a generally horizontal position with optical axis 15 of LMSR device 10 and eye 5 in a vertical treatment-ready configuration with adjunct diagnostic or treatment apparatus 22 in phantom view. Such a vertical position in FIG. 6 of axis 15 corresponds to a eye treatment position of a LASIK or PRK procedure.

Figure 7:
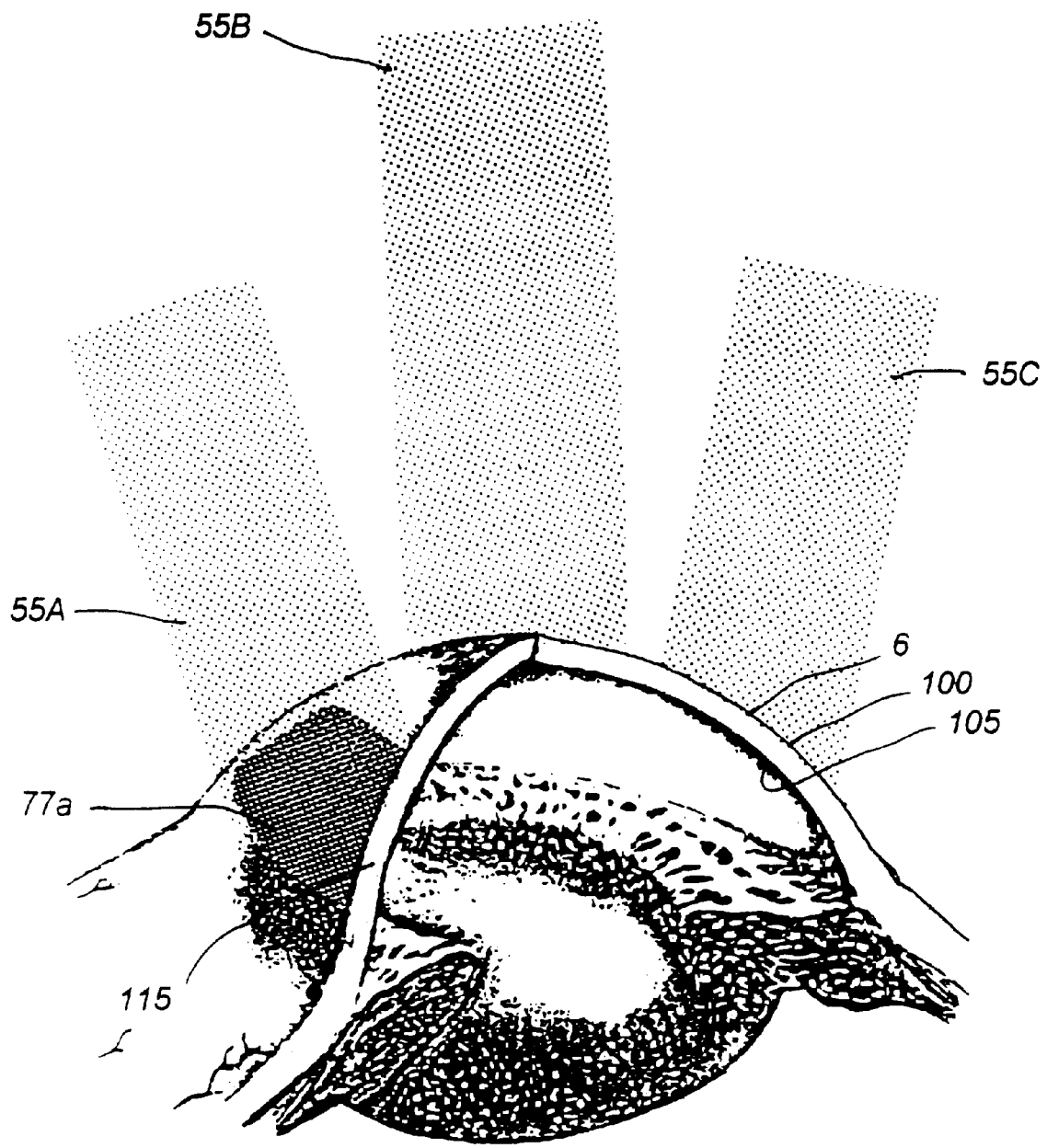
FIG. 7 is a partial sectional view of the eye of FIG. 5 together with three emitters of FIG. 5 showing three emitted beams and a scheme of spatial application of the beams on the anterior surface of the cornea with the human eye in a treatment position as in a LASIK or PRK procedure.
Figure 8A:
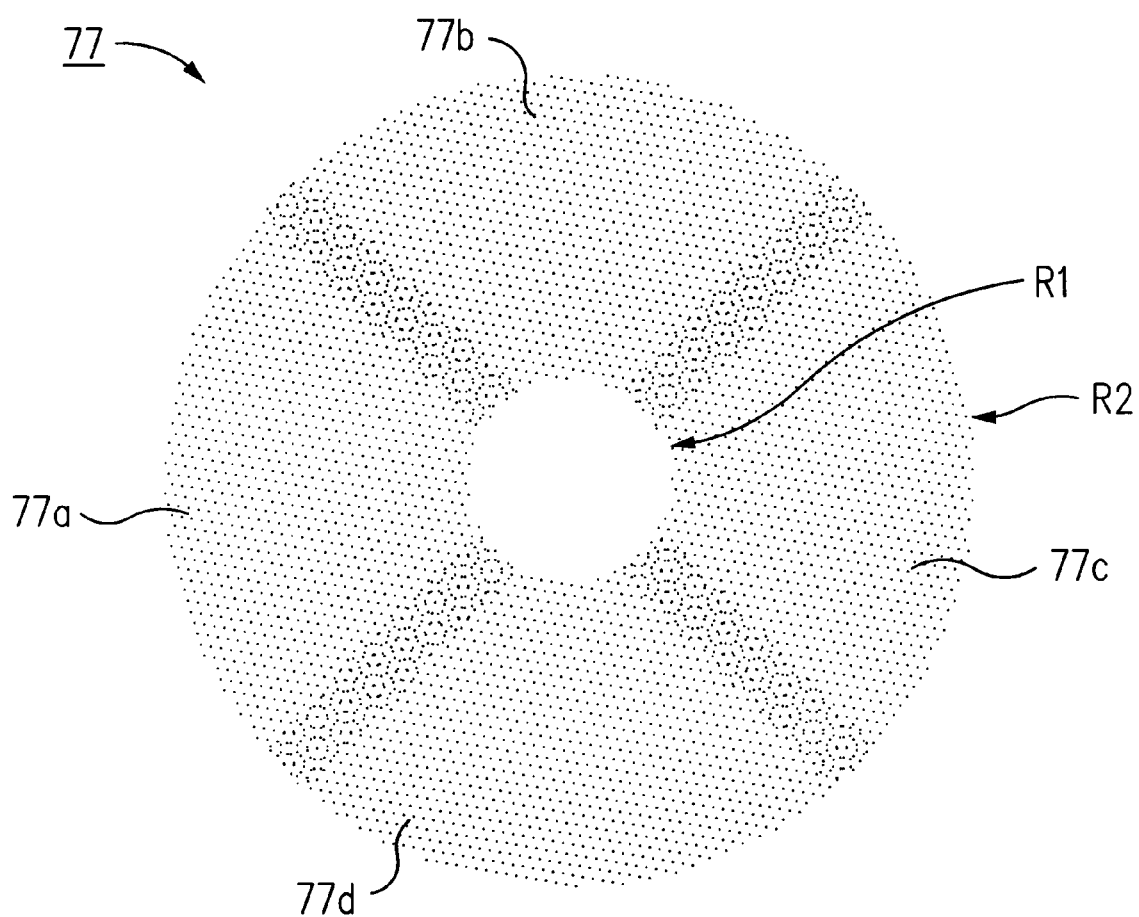
FIG. 8A is a plan view of the patient's cornea the showing the zones in which the photonic energy beams from the emitters of FIG. 5 may scan angular sections thereof.
Figure 8B:
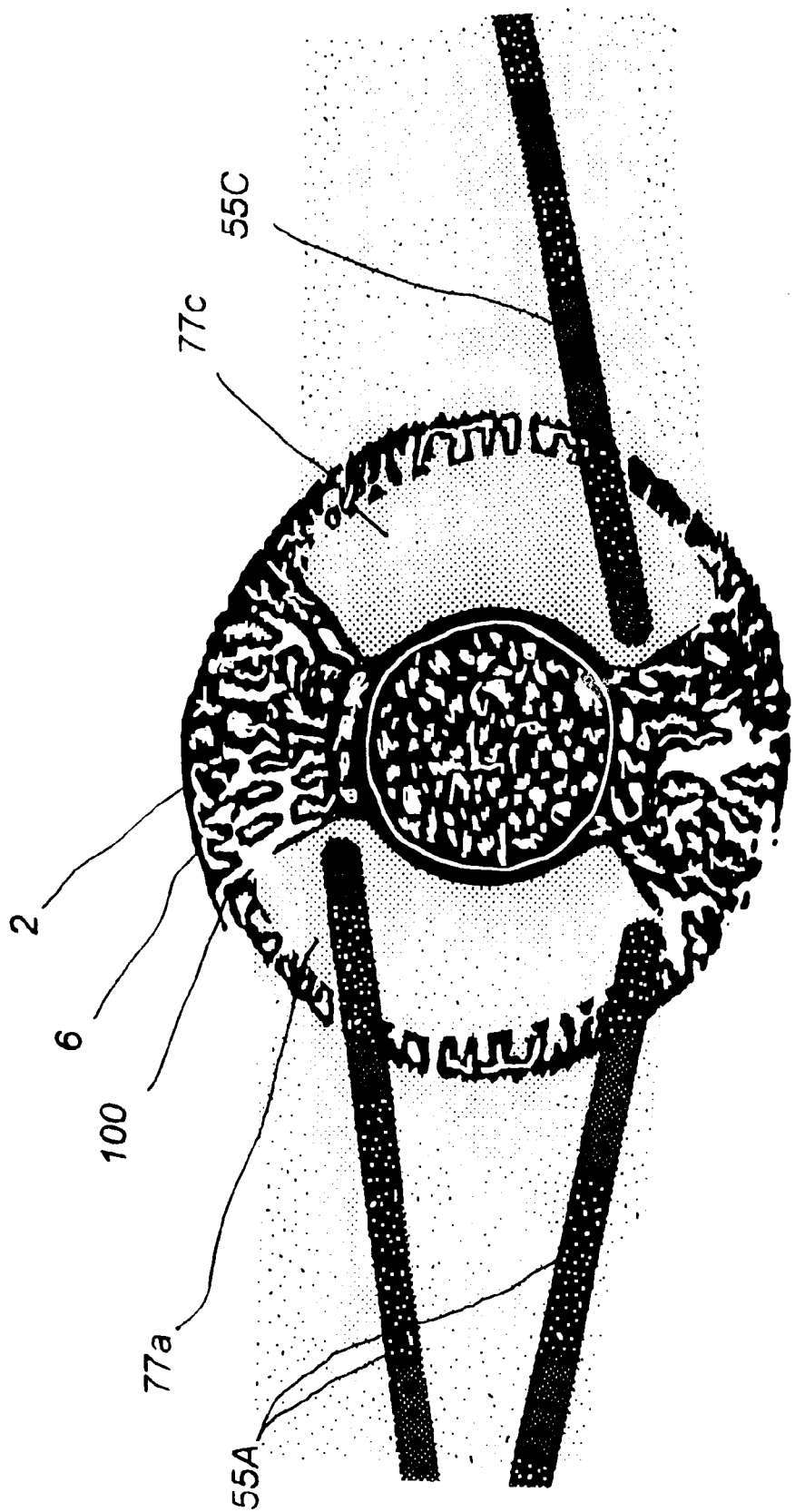
FIG. 8B is view of showing two quadrants of the patient's cornea and underlying iris along with beams from two emitters of FIG. 5.

Referring now to FIGS. 7 and 8A–8B, other views of the spatial application (SA) or beam targeting system are shown. FIG. 8A is a view of the targeted treatment zone 77 on the anterior surface of a cornea. The outer perimeter of zone 77 has about a 10 mm. to 12 mm. diameter around the eye's axis 15. In other words, the collective treatment zone 77 in made up of a number (N) of sectors or quadrants (77a–77d) on the anterior corneal surface. Collective zone 77, as both a limit on the SA system of device 10 and of the method of the invention, thus is an annular shape or ring about the optical axis 15 of an eye with an inner diameter typically being about 1.0 mm. (or as little as zero as when spatial application covers visual axis 15). In sum, the zones 77a–77d (or N angular sectors) of the annular shape scanned thus are covered by the N photonic beams from the N individual emitters, where N equals from 2 to 10, and preferably is 2 to 4. Further, each individual N angular segment is targeted with a beam (55A–55D) from an emitter (50A–50D) that is oriented at an approximate perpendicular angle to the anterior corneal surface cornea in a central portion of the particular treatment zone.

Figure 8C:
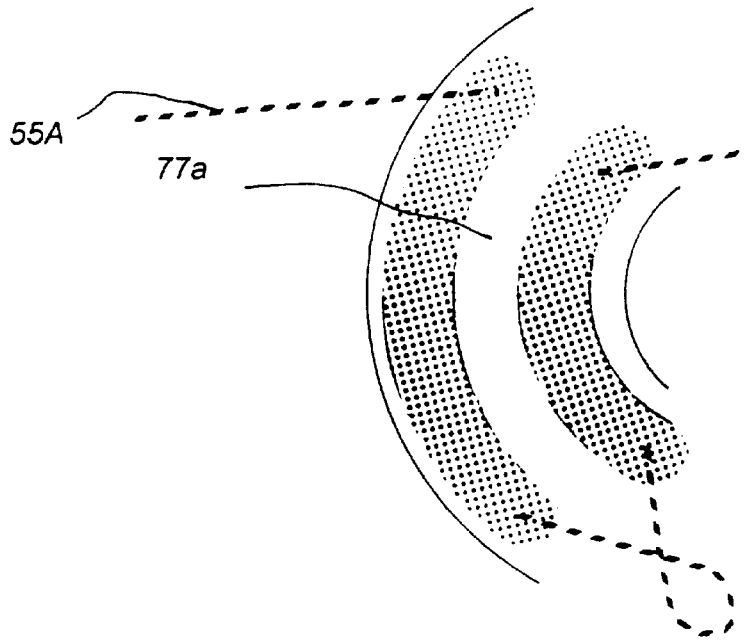
FIG. 8C is view of the quadrant of the patient's cornea indicating a vector scan mode of spatial application of a beam from an emitter of FIG. 5.
Figure 8D:
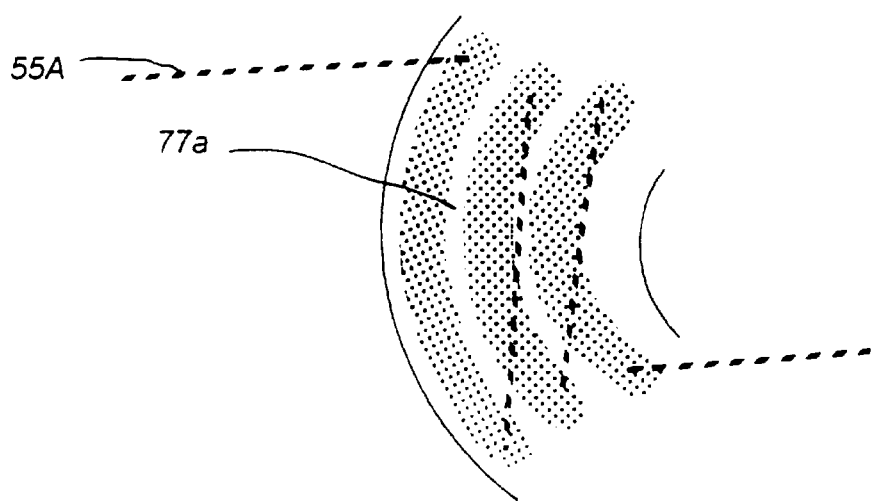
FIG. 8D is view of the quadrant similar to FIG. 8A cornea indicating a raster scan mode of spatial application of a beam from an emitter of FIG. 5.
Figure 8E:
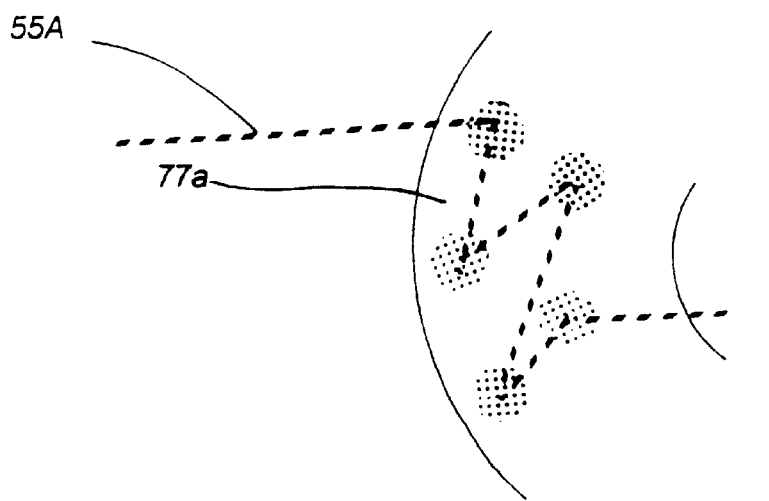
FIG. 8E is view of the quadrant similar to FIG. 8A cornea indicating a step scan mode of spatial application of a beam from an emitter of FIG. 5.

For purposes of explanation, FIG. 8B shows just two opposing photonic beams 55A and 55C in the process of scanning within zones 77a and 77c and incident on anterior corneal surface. Each particular scanner 70A–70D (FIG. 5) is adapted to scan and thus emit a beam in a particular plan, pattern or shape within zone 77a–77d. For example, FIG. 8C represents a vector scan mode of applying beam 55A over quadrant 77a. FIG. 8D represents a raster scan mode of applying the beam over quadrant 77a. FIG. 8E represents a step scan mode of applying the beam over or about quadrant 77a. The zone of treatment targeted by the method of LMSR device 10 is controlled by a computer system operatively connected to each scanner 70A–70E which directs each beam within each zone generally from angle β outside corridor 20 described previously about axis 15 of eye 5. As mentioned above, LMSR device 10 is allowed to operate in a "concurrent treatment mode" with another cooperating apparatus or method (diagnostic or therapeutic procedure), and more particularly to a cooperating topographic imaging system. By the terminology "concurrent treatment mode", it is meant that the patient may be treated with the LMSR device in the treatment-ready position (i.e., at a slit lamp for diagnostic treatment or in a reclining position as in LASIK therapeutic treatment) without having to relocate the patient to another treatment position, no matter whether that LMSR device is actuated prior to, concurrent with, or following the cooperating procedure. The concurrent treatment mode also may be an adjunct to a laser refractive therapeutic treatment (e.g., LASIK or PRK) along corridor 20.

Figure 9:
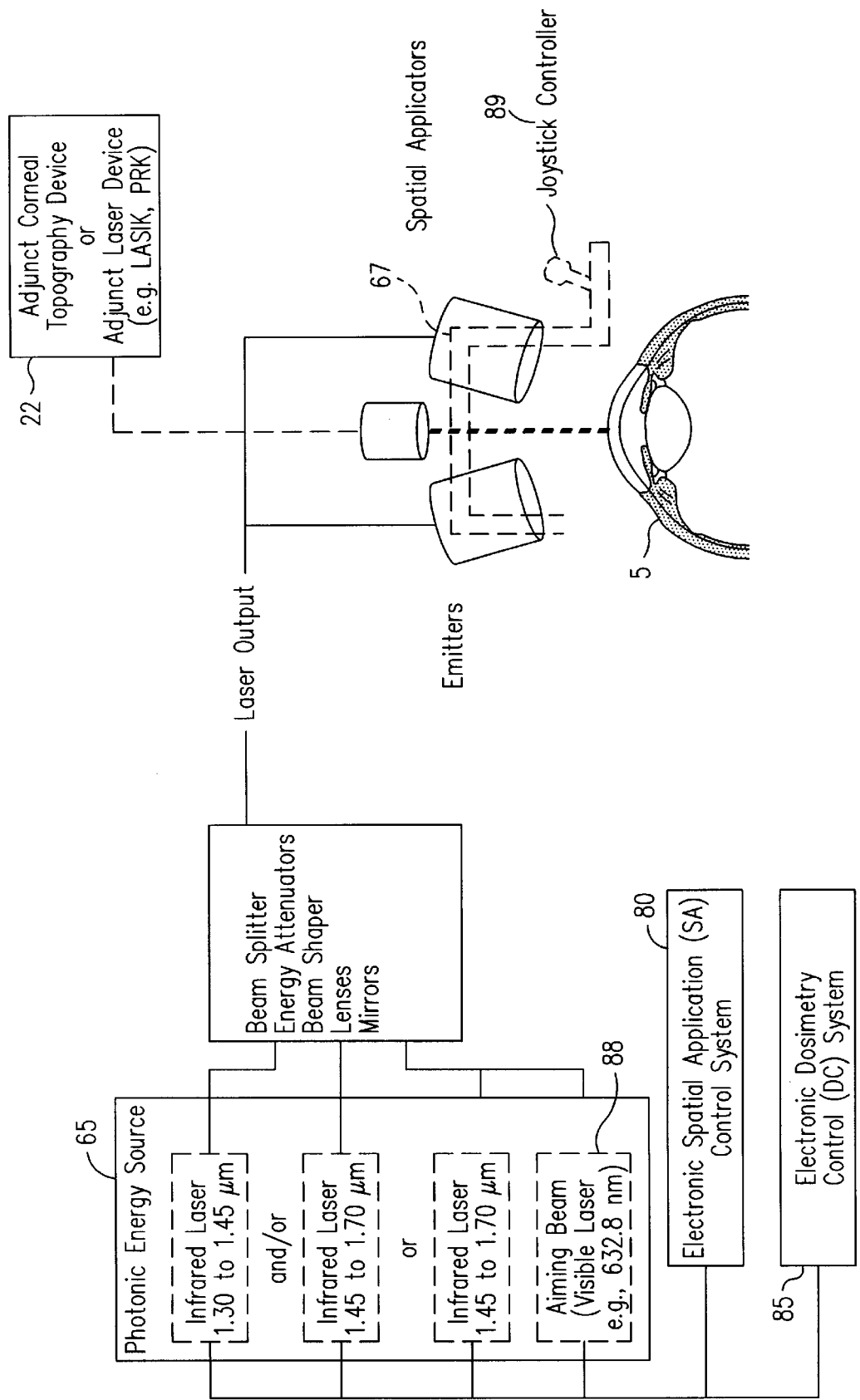
FIG. 9 is block diagram of the components and control systems of the invention of FIG. 5.

Referring to FIG. 9, a block diagram indicates hardware and software of the invention which includes a SA (spatial applicator) control system 80 to control the travel of scanners 70A–70B within emitters 50A–50B in any pattern, or combination thereof, shown in FIGS. 8C–8E. The SA controller 80 is adapted to operate with a dosimetry control (DC) system 85 described below to control the timing and power of the beams generated by photonic energy source 65. It should be appreciated that the scanned portion of each scanned quadrant 77a77d may overlap slightly at ends or sides of adjacent zones (FIG. 8A) but the scan program would prevent any two beams (55A–55D) from overlapping simultaneously which could cause too high of an energy density for the lamellar strain relaxation method described next. The system may further include a visible aiming beam (e.g., a HeNe laser indicted at 88 operating at 632.8 nm or any other suitable visible laser; and a joystick controller 89 as is known in the art for moving the system relative to the patient's eye 5.

2. Beam Wavelength Selection and Method of Lamellar Strain Relaxation. Whereas the preceding section described means for controlling spatial application of radiative energy beams over the anterior corneal surface, this section and FIGS. 10A–10G describe the manner of controlling absorption of the photonic beams in stromal lamellae belong such anterior corneal surface.

Figure 10A:
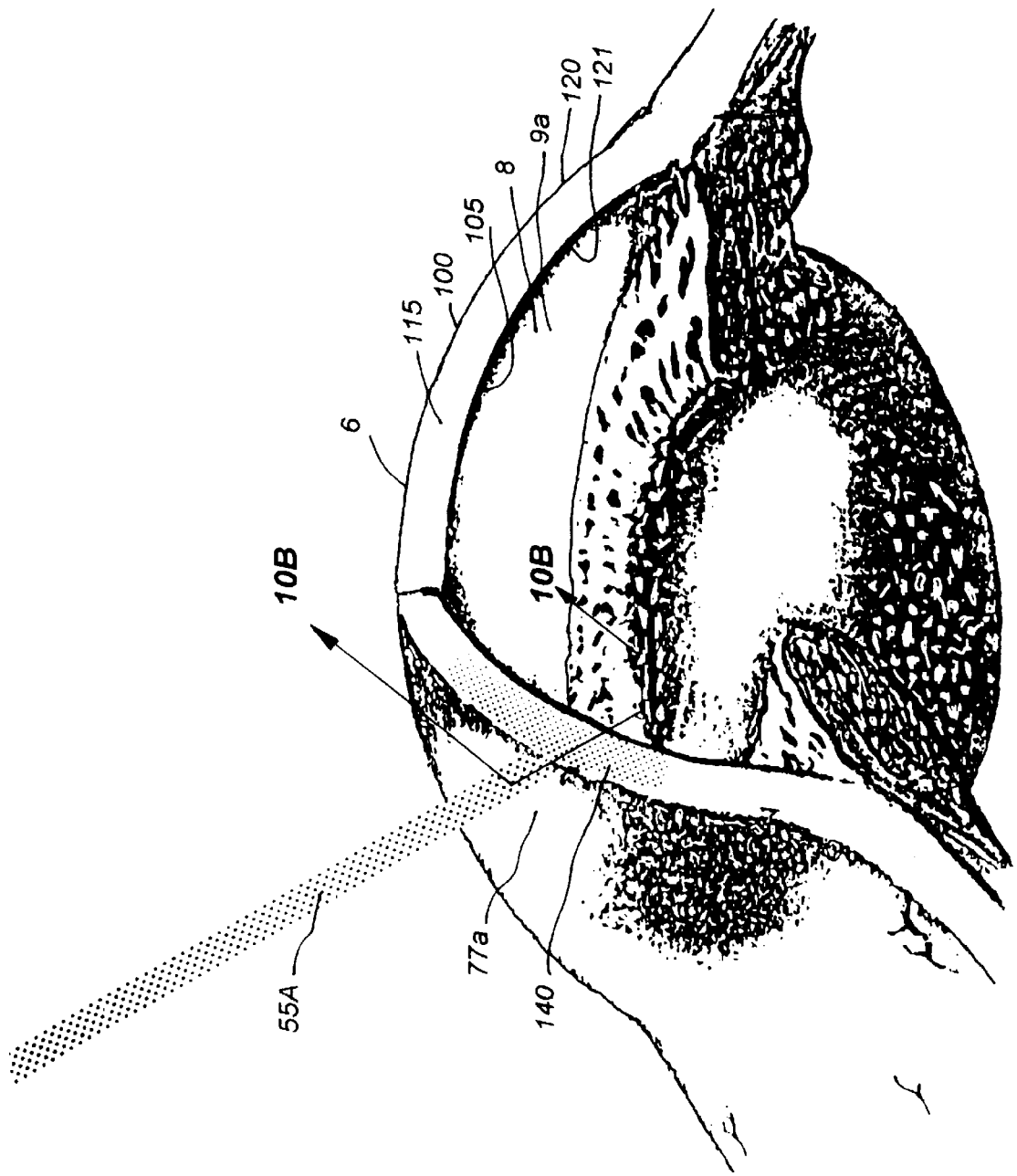
FIGS. 10A–10E are sectional representations of a patients cornea depicting a manner of utilizing the apparatus of FIG. 5 in performing a method of the invention in elevating the temperature of a patient's stroma to relax intra-lamellar strains.
Figure 10B:
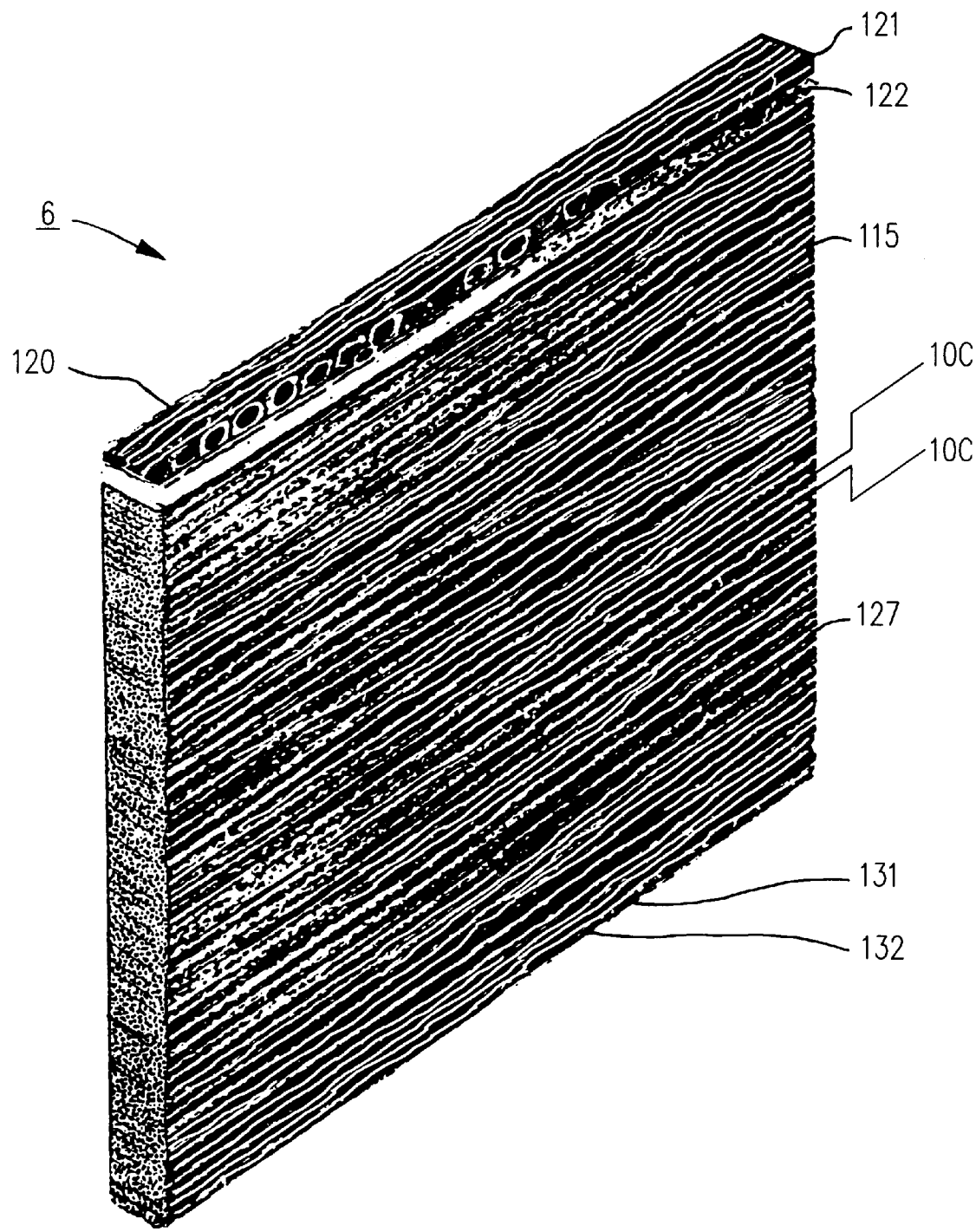

Turning now to FIGS. 10A–10B, a perspective and partial sectional view of eye 5 are shown with beams 55A incident on zone 77a at a particular moment in any method of spatial application of the beams described above. FIG. 10B shows an enlarged full-thickness sectional view of cornea 6 with anterior surface 100 and posterior surface 105. It can be seen that stroma 115 comprises a number of distinct layers which together total a corneal thickness ranging from about 500 to 650 microns at the center and from 1000 to 1200 microns at its periphery (at a diameter from 12 mm. to 15 mm. about axis 15). FIG. 10B shows epithelium 120 which is several cells thick and is smooth and comprises the clear outer surface of the eye that is exposed to the environment. A tear film (not shown) covers the epithelium. The epithelium 120 has a thickness of about 50 microns. Beneath the epithelium is a basal membrane 121 (or basement membrane of epithelium) and Bowman's membrane 122, which together total about 5 to 20 microns in thickness. Bowman's membrane 122 plays a significant role in the morphology of the cornea because it contributes significant tensile strength that contains the stromal lamellae and resists intraocular pressure (IOP) of aqueous humor 9a in anterior chamber 8. In implementing any refractive corrective strategy, it is considered very important to preserve the basement membrane and Bowman's membrane, 121 and 122, substantially intact, for any damage to the epithelium will be quickly corrected by epithelial cellular regeneration.

Figure 10C:
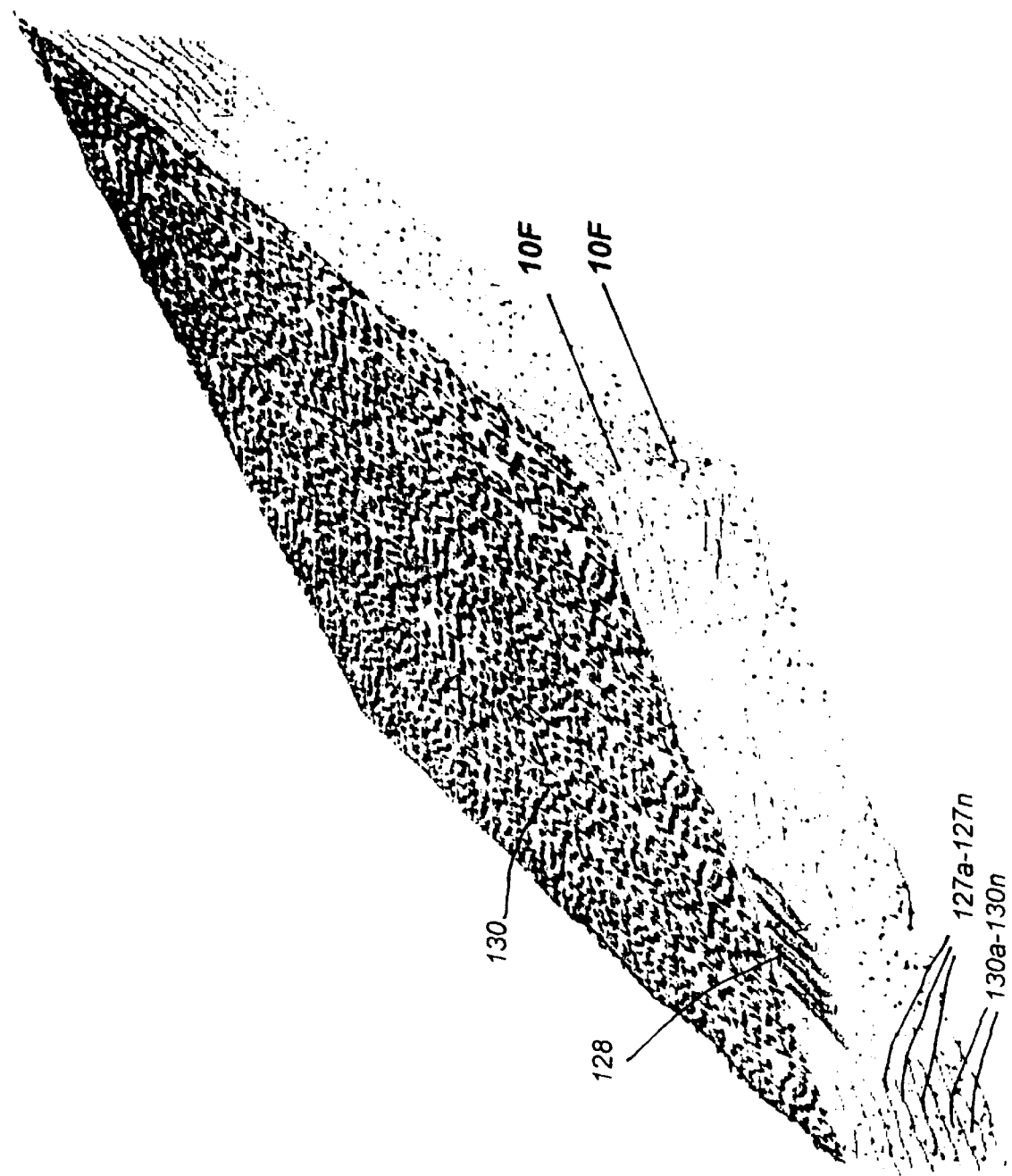

The stroma 115 comprises up to 90–95 percent of the corneal thickness. FIGS. 10B–10C show that stroma 115 is comprised of up to 500 thin layered sheets or lamellae 127 (collectively 127, or individually 127a . . . 127n), each layer containing collagen fibers 128 surrounded by a mucopolysaccharide (MPS) and glycoprotein matrix, collectively called GAGs or ground substance 129 herein. Interleaved between the lamellae 127 are keratocyte layers 130 (collectively 130, or individually 130a . . . 130n) the constitutive cell of the stroma which synthesize the collagen molecules and the GAGs 129 and are shown in distinct layers in FIGS. 10C and 10F. Such keratocyte layers 130 are shown in such manner as they relate to an important aspect of the method of the invention. It is an important objective of the method to elevate temperature levels in lamellae 127 and keratocyte layers 130 to initiate strain relaxation without significant death of keratocytes, for excessive cell death could stimulate an inflammatory or wound healing response which would have unpredictable effects on the lamellar strain relaxation objectives. Beneath stroma 115 are two other layers: Descemet's membrane 131 and the endothelium 132. Descemet's membrane has a thickness of about 7 microns and endothelial layer 132 comprises a single layer of cells having a thickness of about five microns. Stroma 115 is composed of about 75%–80% water by weight.

Figures 1A, 1B:
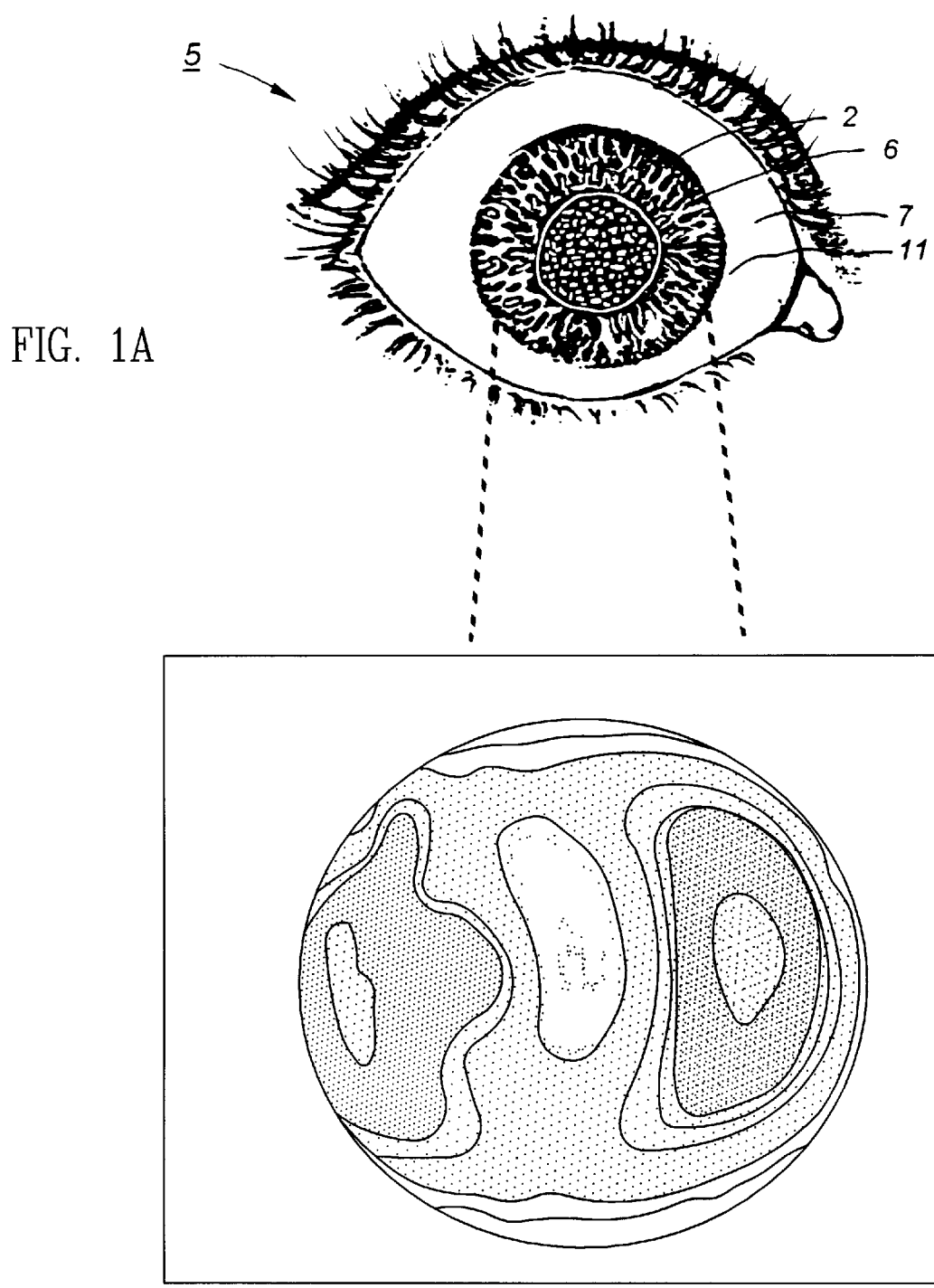
FIGS. 1A–1B are representations of patient's eye together with a topographic map of the anterior surface of the cornea.
Figures 2A, 2B:
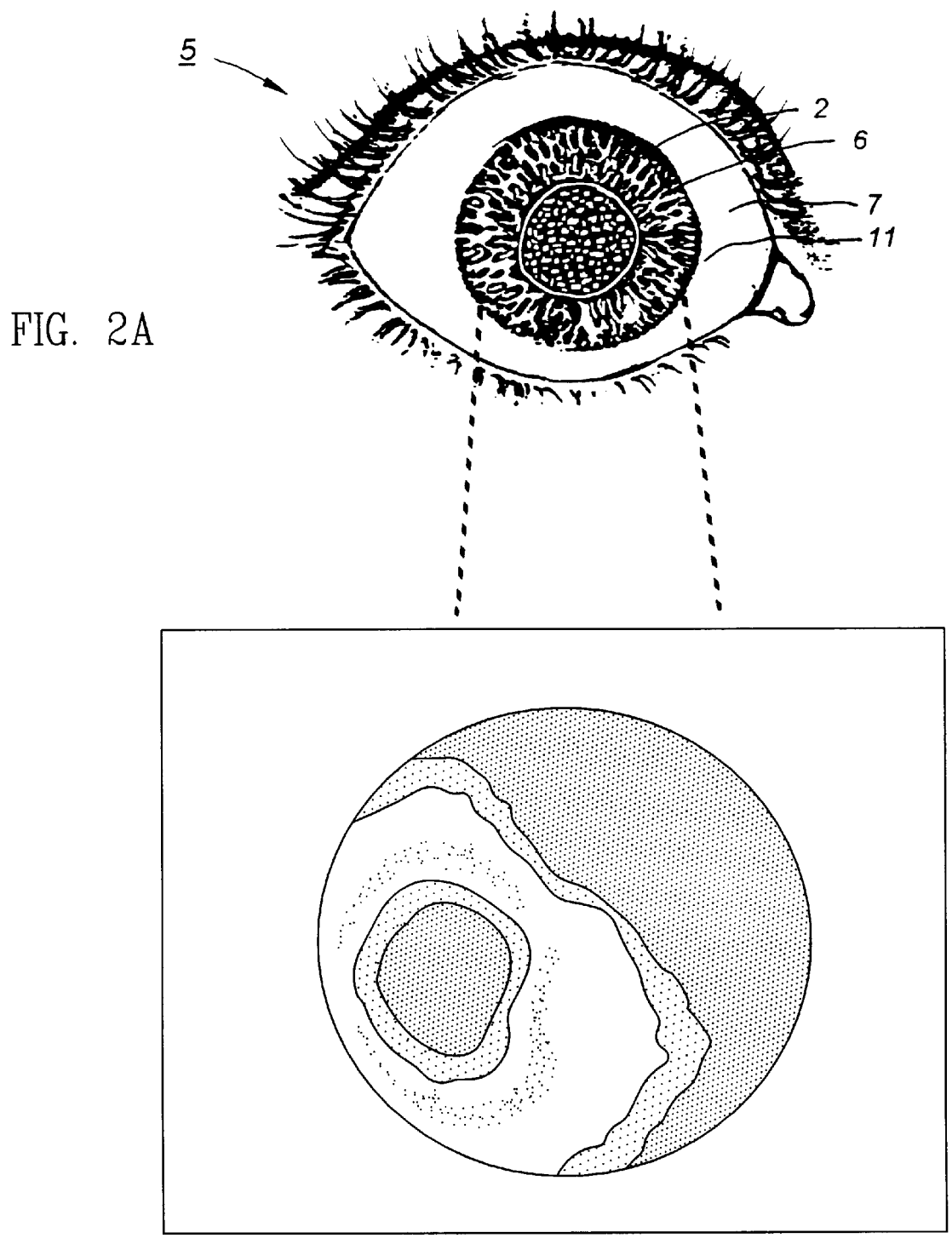
FIGS. 2A–2B are representations of the eye of FIG. 1A and a topographic map of the posterior surface of the cornea.
Figure 3:
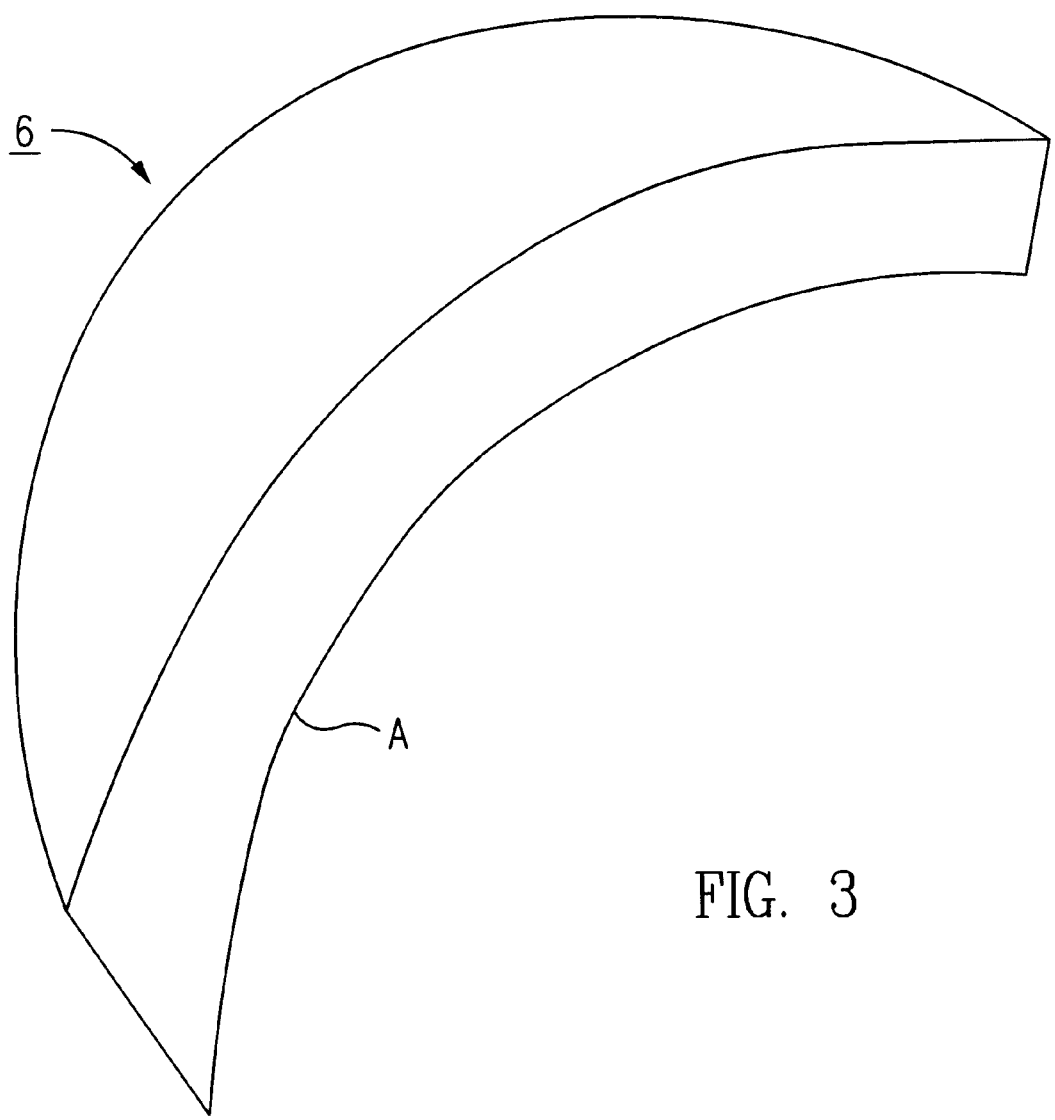
FIG. 3 is a sectional view of the cornea of FIGS. 1A–1B indicating the corneal thickness or pachymetry of the cornea.
Figure 4A:
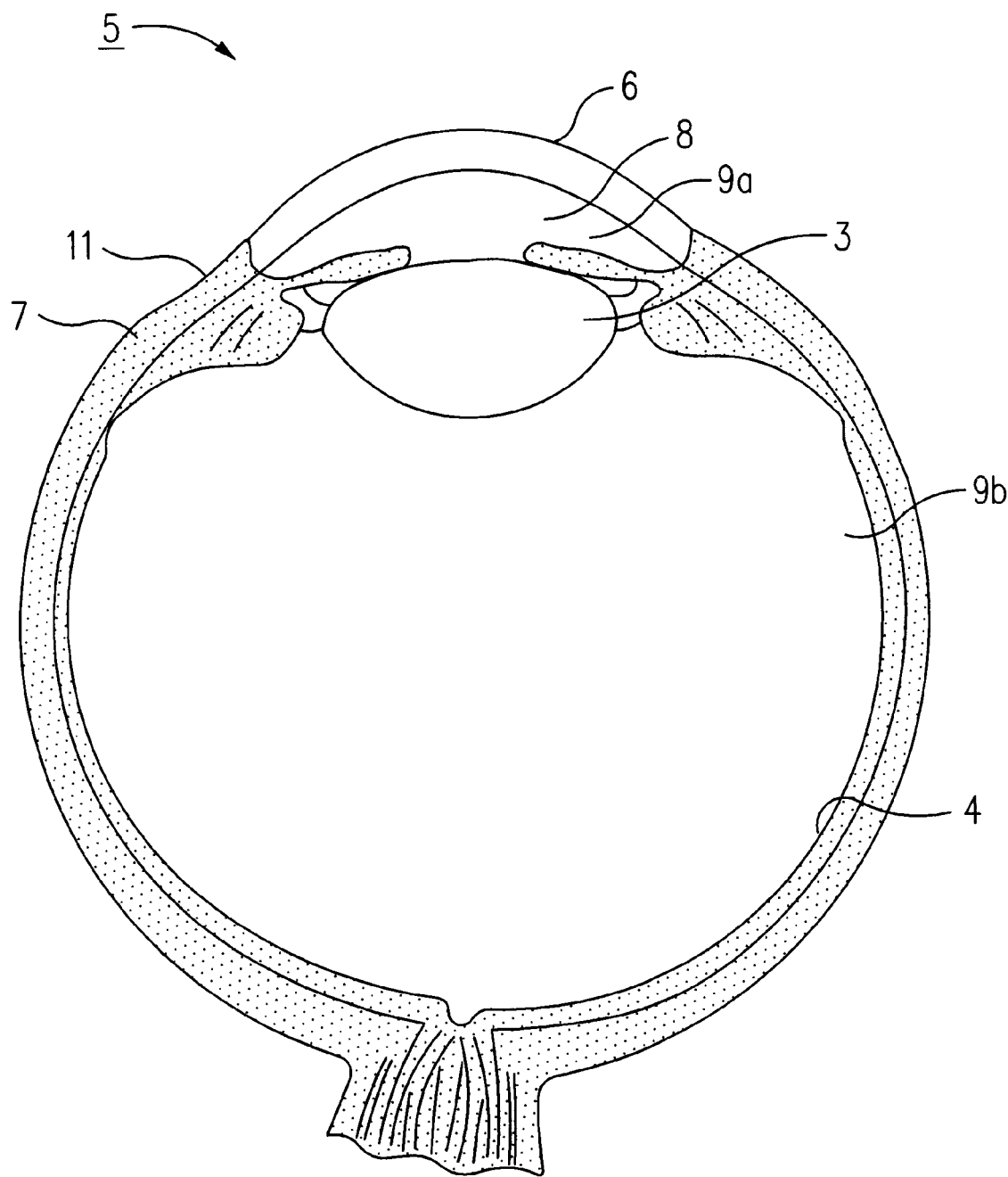
FIG. 4A is a sectional view of a patient's eye showing its anatomy.
Figure 4B:
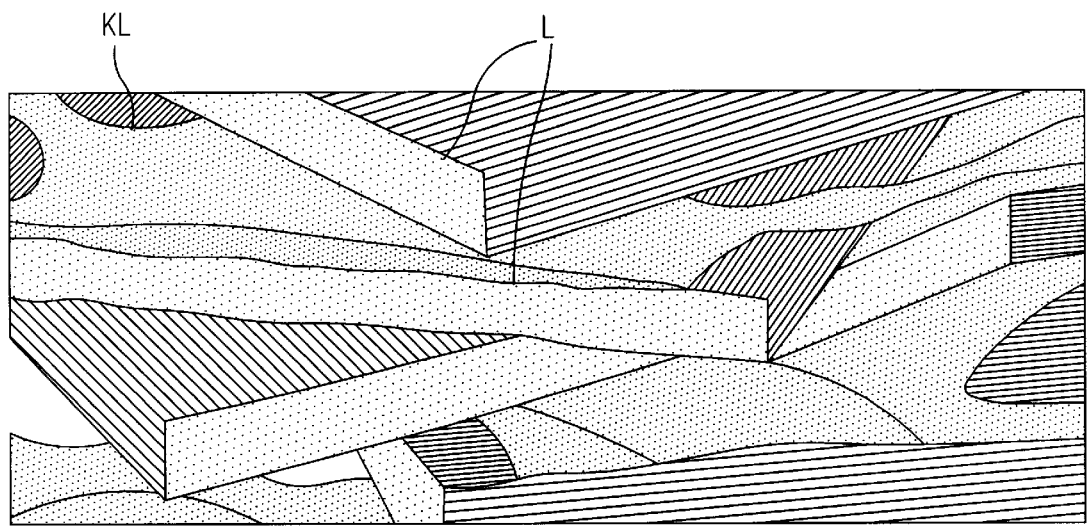
FIG. 4B is a sectional perspective of an interior portion of a cornea showing lamellae and keratocyte layers.
Figure 10E:
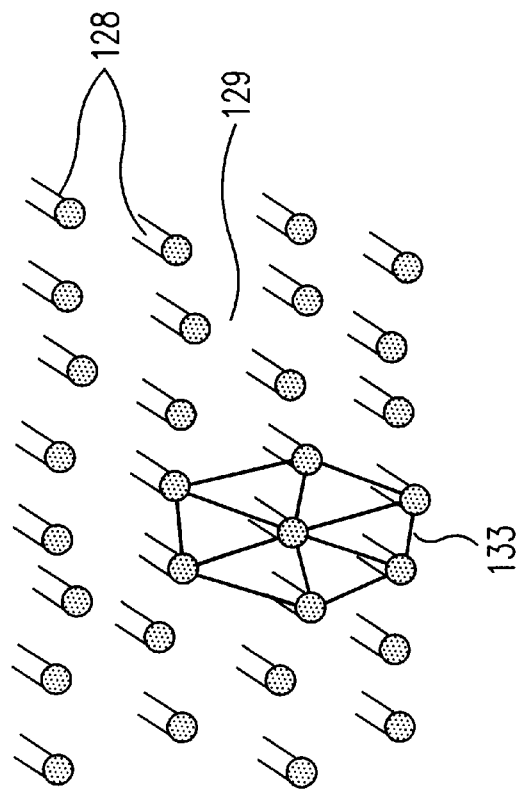
Figure 10D:
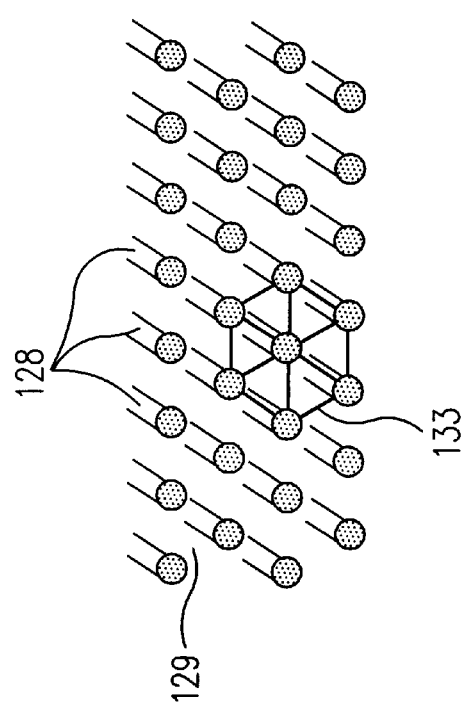

Now turning to FIG. 10C which is a greatly enlarged view the mid-stroma of FIG. 10B showing only about 15–20 lamellae, it can be seen that collagen fibrils 128 extend through the stromal lamellae 127 (see also FIG. 4). The stromal architecture is unusual in that over its 500 microns thickness, the collagen fibrils 128 are arranged in a lattice-like hexagonal structure (see FIGS. 10D and 10E) such that light scattering or internal reflections is eliminated by mutual interference from surrounding individual fibrils. This lattice-like arrangement thus provide corneal clarity and transparency, while at the same time allowing the collagen fibrils to provide tensile strength to contain IOP. FIG. 10E indicates a disrupted arrangement of collagen fibrils that would cause internal scattering and make the corneal nontransparent. The GAGs 129 contribute forces indicated by arrows 133 in FIGS. 10D–10E that both resist compression of 128 fibrils together and resist expansion of the fibrils apart which forces are linked to the corneal dehydration mechanism described above.

The collagen fibrils in the stroma 115 are made up of molecules having a triple helix of proteins about 300 nm. in length, wherein the types of amino acids in the proteins define type of collagen, for example, Type I collagen forming the principal type in the stroma. Collagen molecules are organized into small bundles of about five molecules called microfibrils, wherein the collagen molecules align with one another but offset about one-fourth of the molecular length. These microfibrils further are arranged into larger diameter and longer structural units called fibrils. Covalent cross-links exist between the three proteins of the triple helix and between the collagen molecules making up the micro-fibrils. These cross-links provide stability to the triple-helix molecules as well as (i) resisting mechanical strains on the micro-fibrils and fibrils and (ii) resisting temperature stresses on the molecules, micro-fibrils and fibrils. The stromal collagen fibrils 128 within lamellae 127 are only about 25–35 nm in diameter but extend as much as 10 mm. across cornea from limbus to limbus 11. The very small diameter of the corneal fibrils allow the for transparency and may be contrasted with collagen fibrils of sclera 7, which randomly vary in diameter from about 25–250 nm. which cause internal photon scattering and renders the sclera 104 white in color (see FIGS. 10D–10E).

Now referring back to FIG. 10A, the shaded area indicted at 140 is the depth region of stroma 115 that is targeted for thermal-mediated strain relaxation, although it should be appreciated that more precise depth ranges may be targeted. Such strain relief requires the selection of a particular range of light wavelengths from photonic source 65 via emitters 50A–50D. As background, it must be understood that when photonic energy (e.g., a coherent or non-coherent light energy beam) is incident upon tissue, five effects may result: (i) the beam, or some or all of the photons thereof, may be reflected off the tissue surface; (ii) the photons thereof may be transmitted entirely through the tissue medium, (iii) the photons thereof may be absorbed along the beam's path in a medium by absorption within an identifiable chromophore (e.g., a pigment), (iv) the photons thereof may be absorbed along the beam's path by varied processes of scattering; or (v) some of beam may be scattered within the tissue beyond the region of the beam's path as it propagates within the tissue medium.

Several of the above factors are of interest to the method of the invention to achieve its objective of relieving lamellar strains and other stresses. First, in order to minimize photonic beam reflection off anterior surface 100 of cornea 6 to the maximum extent possible, the emitters 50A–50D have axes 57a–57n that are defined by the ranges of angle β relative to optical axis 15 described above (see FIG. 6). In other words, the emitter axes 57a–57d in their repose positions are adapted to be substantially perpendicular to anterior surface 100 of cornea 6 as described previously to prevent such reflection.

Of particular interest to optimizing lamellar strain relaxation are the photon absorption effects (iii) and (iv) described above which will elevate the temperature of the lamellae 127 and interleaved keratocyte layers 130 to achieve a desired effect. Preferably, the photons of the radiative beam will be absorbed by $H_2O$ in stroma 115 acting as a chromophore, and also be absorbed by photon scattering processes (i.e., Mie scattering and Rayleigh scattering) within a significant depth of the stroma, for example within about the first two-thirds to three-fourths of the depth of the cornea (i.e., about 350 to 450 microns) which is indicated at 140 in FIG. 10B. By this means, a significant effect on lamellae 127 (collagen 128 and GAGs 129) and keratocyte layers 130 will thermally relax osmotic forces and other strains in the cornea, which were in part described in the Background of the Invention section above. At the same time, it is important that the thermally-mediated lamellar relaxation treatment does not elevate endothelial layer 132 to a significant extent. Also, it is important that the thermally-mediated relaxation treatment not cause significant keratocyte death which could induce an inflammatory or wound healing response. FIG. 10A thus illustrates that the targeted region of photonic energy absorption in substantially the entire thickness of the cornea to effect the method of the invention. The preferred target temperature of the stromal region is within a range of about 42°–58° C. for a period of time ranging from about 1 second to 120 seconds. More preferably, the target temperature is within a range of 44° to 54° C. Still more preferably, the target temperature is within a range of 46° to 52° C. The optimal therapeutic effects will result from a balance of appropriate light energy wavelength, power level and exposure duration (the length of exposure relating to scanning paths and speeds).

Figure 11:
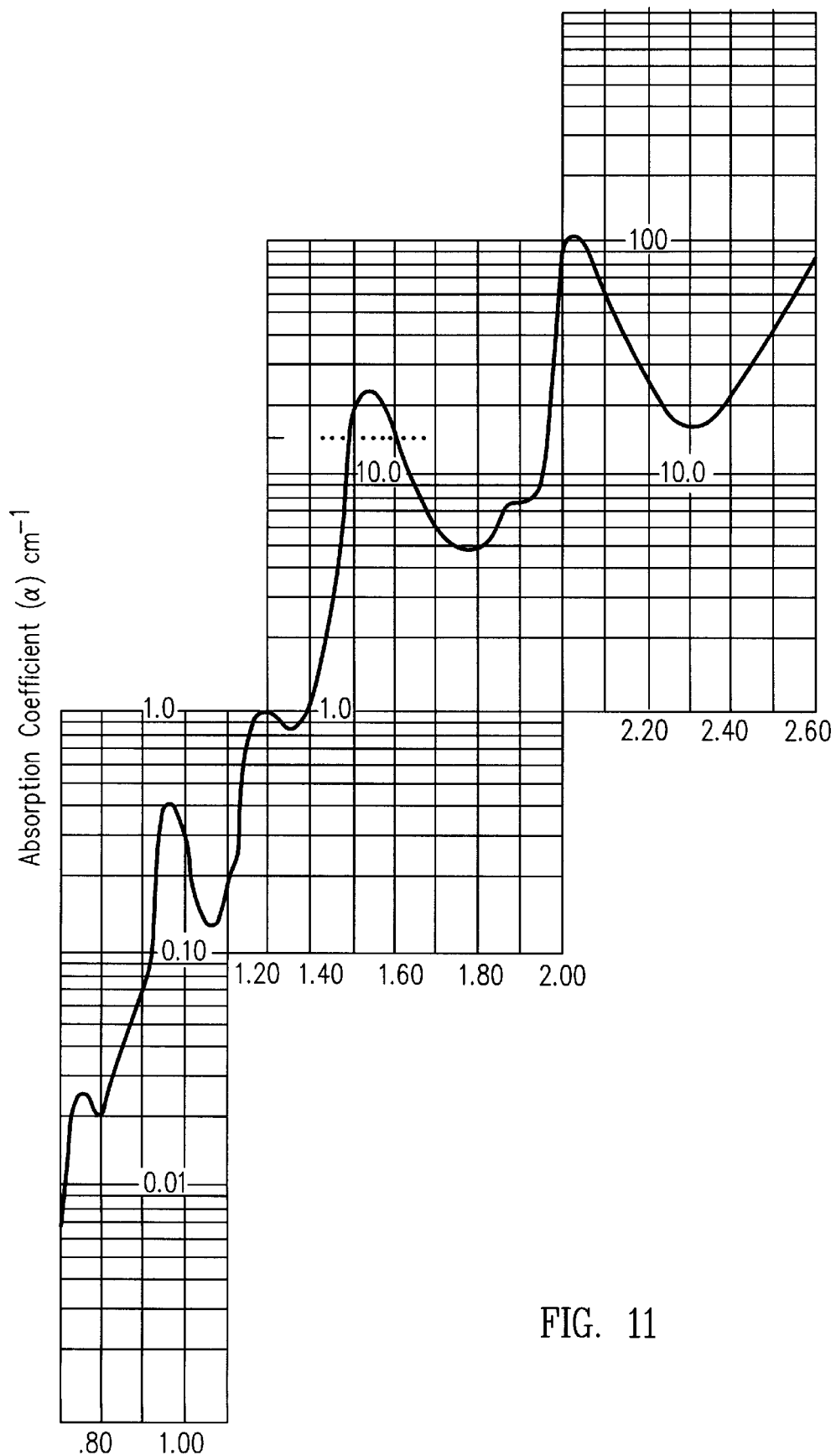
FIG. 11 is a graph showing light wavelengths with absorption coefficients in water.

Approximately 90 percent of incident photon energy of a particular wavelength is absorbed in tissue a characteristic "length of travel", which is termed an extinction length which is wavelength dependent. Another commonly utilized term, which relates again to a measure of photon absorption is the "absorption length", which is a distance over which 63 percent of the light is absorbed. Since the stroma is about 75%–80% water with little cellular pigmentation, FIG. 11 is relevant as it depicts an absorption coefficient of water as a function of wavelength ($\lambda$). As can be seen in FIG. 11, the absorption coefficient of water varies by a factor of about 10,000,000 from a peak light transmission where $\lambda$=500 nm. in the visible spectrum to peak light absorption where $\lambda$=at 2.8 $\mu$m in the infrared portion of the spectrum.

By means of research and calculations with wavelengths having known absorption coefficients, it is postulated that the preferred wavelength range for light-mediated lamellar strain relaxation (coherent or non-coherent) lies in the near-infrared portion of the spectrum, the source 65 preferably radiating at a wavelength of from about 1.32 to 1.70 microns ($\mu$m). For example, a radiative light source 65 having a wavelength from about of 1.32 to 1.70 microns coincides with a somewhat heightened water absorption band. Preferably, such photonic energy would be selected at from 1.44 to 1.55 microns where the absorption coefficient ($\alpha$) in $H_2O$ range between about $\alpha$=32.18 $cm^{-1}$ to 11.65 $cm^{-1}$ and absorbed by water after passing from about 300 to 800 microns therein. It is believed that this range of 1.44 to 1.55 microns will prove best suited for lamellar strain relaxation. Within this wavelength domain, excessive temperature elevation could occur in the endothelial layer when the absorption coefficients are in the range of $\alpha$=+/−20 $cm^{-1}$ to +/−10 $cm^{-1}$. For this reason, the dosimetry control (DC) system described below can be programmed to maintain temperatures well below the maximums of the particular levels described above. The beam widths form photonic energy source 65 may be from about 0.05 mm. to 2.0 mm. or more and are dependent somewhat on scanning paths. Also it should be appreciated that depth-sensitive lamellar strain relaxation may be shown to be effective in the future and should be considered to fall within the scope of the invention. In other words, the use of wavelengths having absorption coefficients (in water) from between about 20 $cm^{-1}$ to 10 $cm^{-1}$ may be adapted for use in the method of the invention to thermally-mediate such strain relaxation (e.g., at temperatures of 42°–52° C.) wherein the absorption depth is deeper in stroma 115. Conversely, wavelengths with absorption coefficients ranging above about 20 $cm^{-1}$ may be best adapted to perform the strain relaxation method (e.g., at target temperatures of 52°–58° C.) wherein the absorption depth is shallower in stroma 115. Thus, an LMSR device that is adapted to deliver two (or more) wavelengths for thermally-relaxing different depths of lamellae 127 is within the scope of the present invention. For example, the first wavelength of the LMSR device may have an absorption coefficient ranging from about $\alpha=20$ $cm^{-1}$ to 10 $cm^{-1}$; the second wavelength having an absorption coefficient ranging from about $\alpha=32$ $cm^{-1}$ to 20 $cm^{-1}$ with two or more light sources operatively connected to the LMSR and adapted to operate concurrently.

Figure 4C:
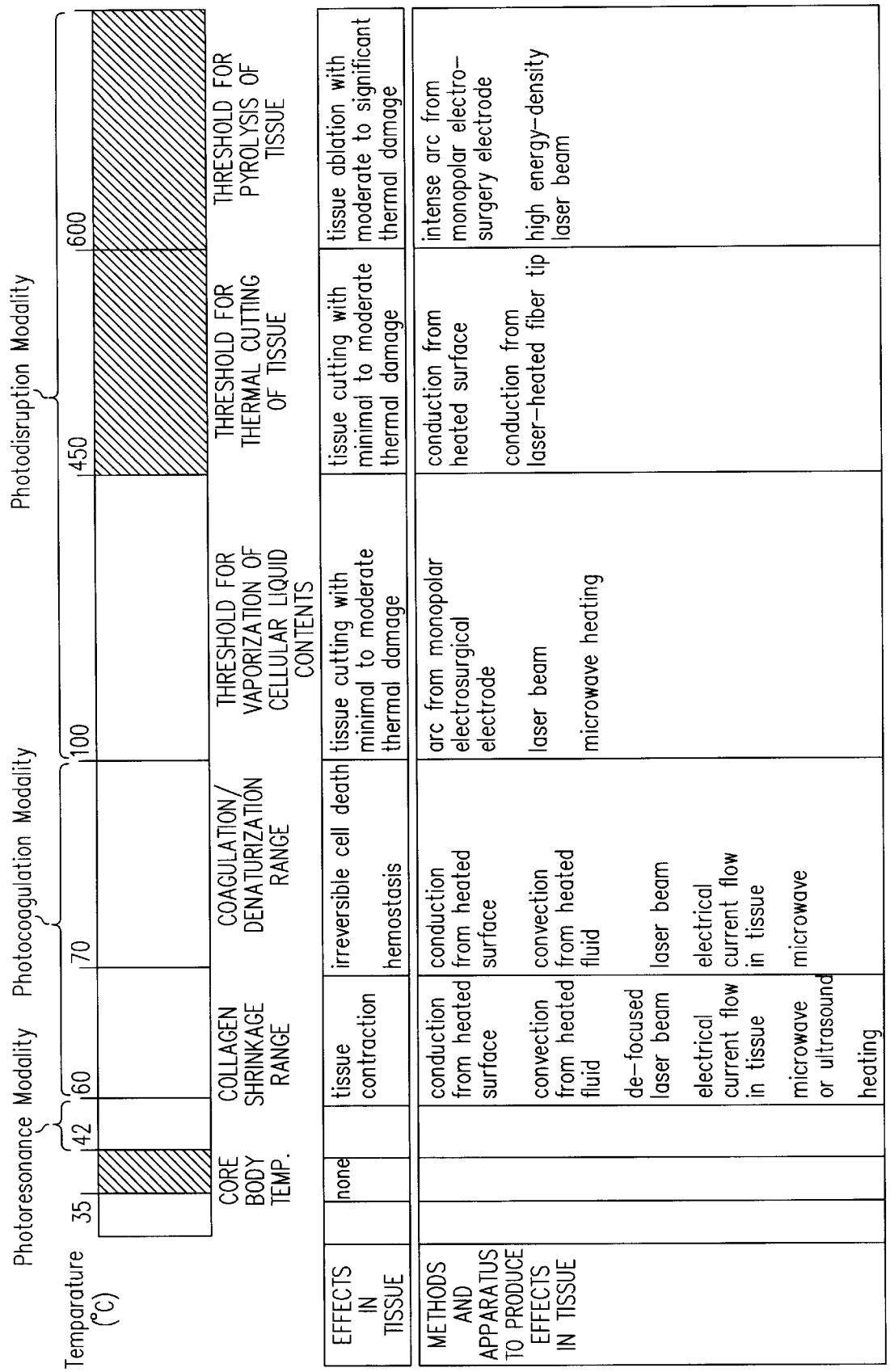
FIG. 4C is a chart indicating the laser-tissue effects caused at various temperature levels in tissue, including the modality of photoresonance of the present invention wherein tissue is elevated in temperature; the photocoagulation modality wherein tissue is caused to coagulate, denature or shrink; and the photodisruption modality wherein tissue is vaporized; the chart further indicating other energy delivery modalities that can cause such tissue effects.

The lamellar strain relaxation modality proposed as the method of the invention herein differs significantly from other typical modalities of photonic-tissue interactions. The most common modality of laser-tissue interaction is the photodisruption modality, wherein photons of a light energy beam disrupts the chemical bonds of atoms or molecules making up the medium, with the end result being that the medium is vaporized as indicated in FIG. 4C. Such energetic photons are found in longer wavelengths, e.g., the 193 nm. wavelengths of the excimer laser used in LASIK and PRK procedures. Another common laser-tissue interaction is termed the photocoagulation modality, wherein photons elevate tissue temperatures sufficient to coagulate, denature, shrink or desiccate tissues (see FIG. 4C). In the present invention, the objective is to elevate stromal temperatures well below those used to practice the photodisruption or photocoagulation modalities. The photoresonation modality proposed herein uses far less energetic photons in the range of 1.32–1.70 microns which will cause atoms and molecules in the stromal medium to resonate or vibrate rapidly. The resonating effect will elevate the temperature within the absorbing medium without disrupting any intramolecular or intermolecular chemical bonds. For example, it is well known that intramolecular and intermolecular bonds can be broken or disrupted at temperatures above about 60° C. which can cause denaturation of stromal collagen fibrils, which are above the temperatures proposed herein. At the higher temperatures, such denaturation of collagen has been commonly referred to as photocoagulation or shrinkage of collagen (see FIG. 4C). For that reason, the lamellar strain relaxation modality is accomplished within the lesser temperature ranges described above, also indicated in FIG. 4C.

A continuous wave (CW) light source, such as a diode laser, is preferred over a pulsed system for reasons that can be explained by the mechanisms of heat transfer in tissue. In the above preferred wavelengths, when the photonic beam is absorbed in tissue medium, both by chromophores and by photon scattering, the energy in the beam is imparted to the absorbing medium or lamellar structure along the path of beam propagation. The photonic energy that is absorbed by the medium heats the absorbing volume instantly, for example in a period ranging from femto-seconds to pico-seconds. Essentially, all of the energy in the photonic beam is deposited in the tissue within about one extinction length. Thus, it can be calculated that a three-dimensional volume of the lamellar medium can be elevated in temperature dependent on (i) the beam diameter, and (ii) the extinction length of the particular wavelength, with some adjustment for scattering. To optimize the lamellar strain relaxation, it is necessary to deposit enough energy into the absorbing volume to elevate the volume to the desired temperature range before it diffuses excessively into surrounding tissue volumes. This process of heat diffusion, called thermal relaxation, is the process of conduction with the absorbing volume's thermal relaxation time (often defined as the time over which photothermal temperature elevation is reduced by one-half). Such thermal relaxation time scales with the square of the diameter of the irradiated absorbing volume in a spherical volume, decreasing as the diameter decreases. For a cylindrical-shaped irradiated volume with diameter d and length l, such thermal relaxation time is determined by the lesser of the two dimensions. In a pulsed energy delivery system, the above wavelengths and absorption coefficients would achieve the desired temperatures for the required period of time, it is believed, only at higher power levels than a CW system since there would be significant heat diffusion between pulses of energy delivery. Such higher energy levels of a pulsed system would probably result in higher peak temperatures which could cause undesirable or excessive cellular death in keratocyte layers 130. A second reason that a CW energy source is preferred is that such a source 65 can eliminate another undesirable effect of short pulses, which is that pulsed photonic energy delivery typically causes photoacoustic shock waves. Such shock waves are to be avoided since they can disrupt lamellae 127 and collagen fibrins 128 therein to a significant extent such that, at any exposure site, the lattice structure of the collagen fibrils would be disordered as in FIG. 10E to temporarily affect corneal transparency. Photoacoustic shock waves can also disrupt or cause keratocyte death which is undesirable for reasons described above. Further, a diode laser as source 65 is compact and can be easily operated by an electronic control system. Such diode sources can operate in the mid-infrared wavelengths described above and can be introduced into an optical fiber easily with losses.

Figure 10F:
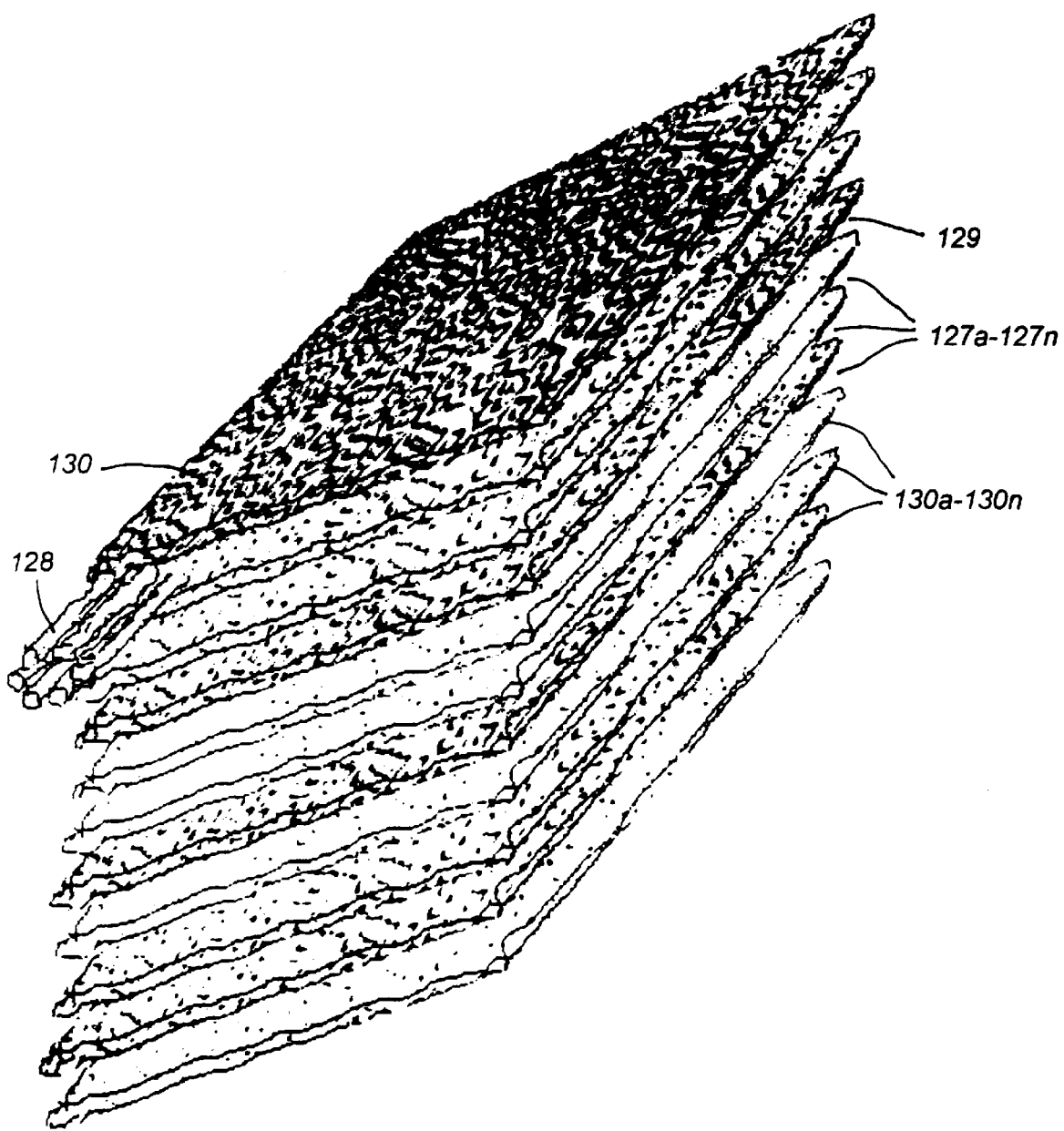
Figure 10G:
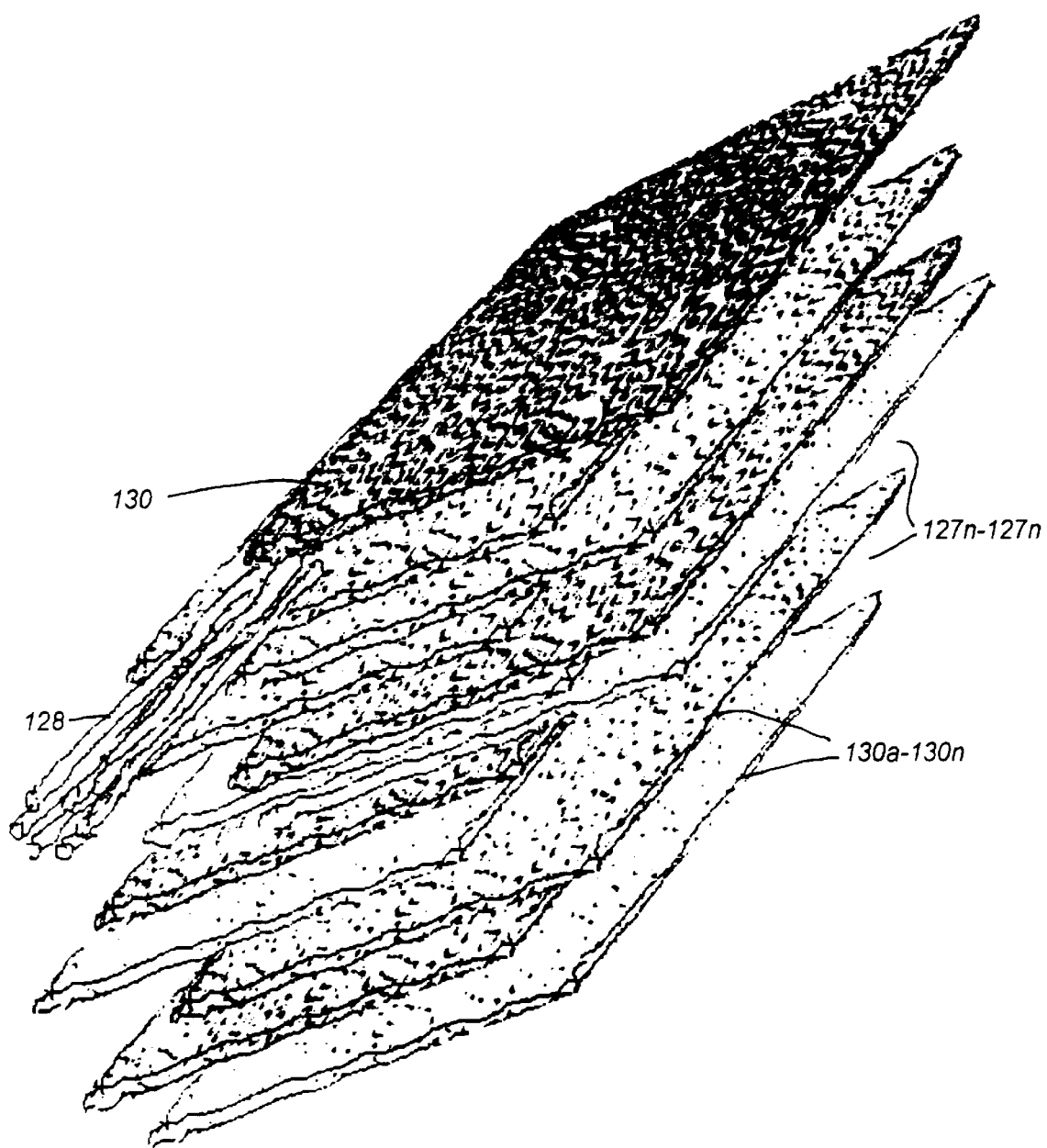

Thus, FIGS. 10F–10G depict the ultimate effect of utilizing device 10 in performing a light-mediated strain relaxation method to release strains and stresses in or among lamellae 127. FIG. 10F is a greatly enlarged sectional view of just a few sheets of lamellae 127a . . . 127n and interleaved keratocytes layers 130a . . . 130n in stroma 115. Collagen fibrils are indicated at 128. FIG. 10F shows the lamellae in a native state prior to treatment or absorption a photonic energy beam. FIG. 10G next shows the lamellar structure immediately following the absorption photons within lamellae 127a . . . 127n and the interleaved keratocytes layers 130a . . . 130n. It is represented that the lamellar structure has shifted and relaxed intrastromal forces due to the thermal effects of the photonic energy beam being absorbed by the corneal medium. Thus, it is believed, such thermal treatment will alter osmotic forces in lamellae 127 and GAGs 129 to alter lamellar morphology and follow-on corneal topography will show an altered—and strain-relaxed—curvature and pachymetry of the cornea.

Referring still to FIG. 10G, it should be appreciated that the lamellae 127a. . . 127n and keratocyte layers 130a . . . 130n shown may result from one or more elevations and relaxations of temperature of the absorbing volume to reduce or relax the biomechanical strains within the volume, which is a method of the invention. Further, the general effects shown in FIG. 10G are intended to apply to relaxation of strains within basement membrane 121 and Bowman's layer 122 (not shown in FIG. 10G) and are within the inventive method. The strain-relaxed topography that follows the treatments indicated in FIGS. 10E–10F will provide better data for follow-on any refractive strategies.

3. Dosimetry Control Component of LMSR Device. The LMSR device includes a dosimetry control (DC) system indicated at 85 in FIG. 9 that is adapted to control timing and power level of photonic energy delivery through emitters 50A–50D in various operational modes. The dosimetry control system can operate in a basic mode of operation wherein a pre-set program is used to control the power level of photonic energy source(s) 65. Such a dosimetry control system 85 is adapted to operate in conjunction with the scanner control (SC) system 80, for example to maintain power at a particular energy level for a particular time interval while scanners 70A–70D moves the incident beams in particular pre-set paths.

Figure 12:
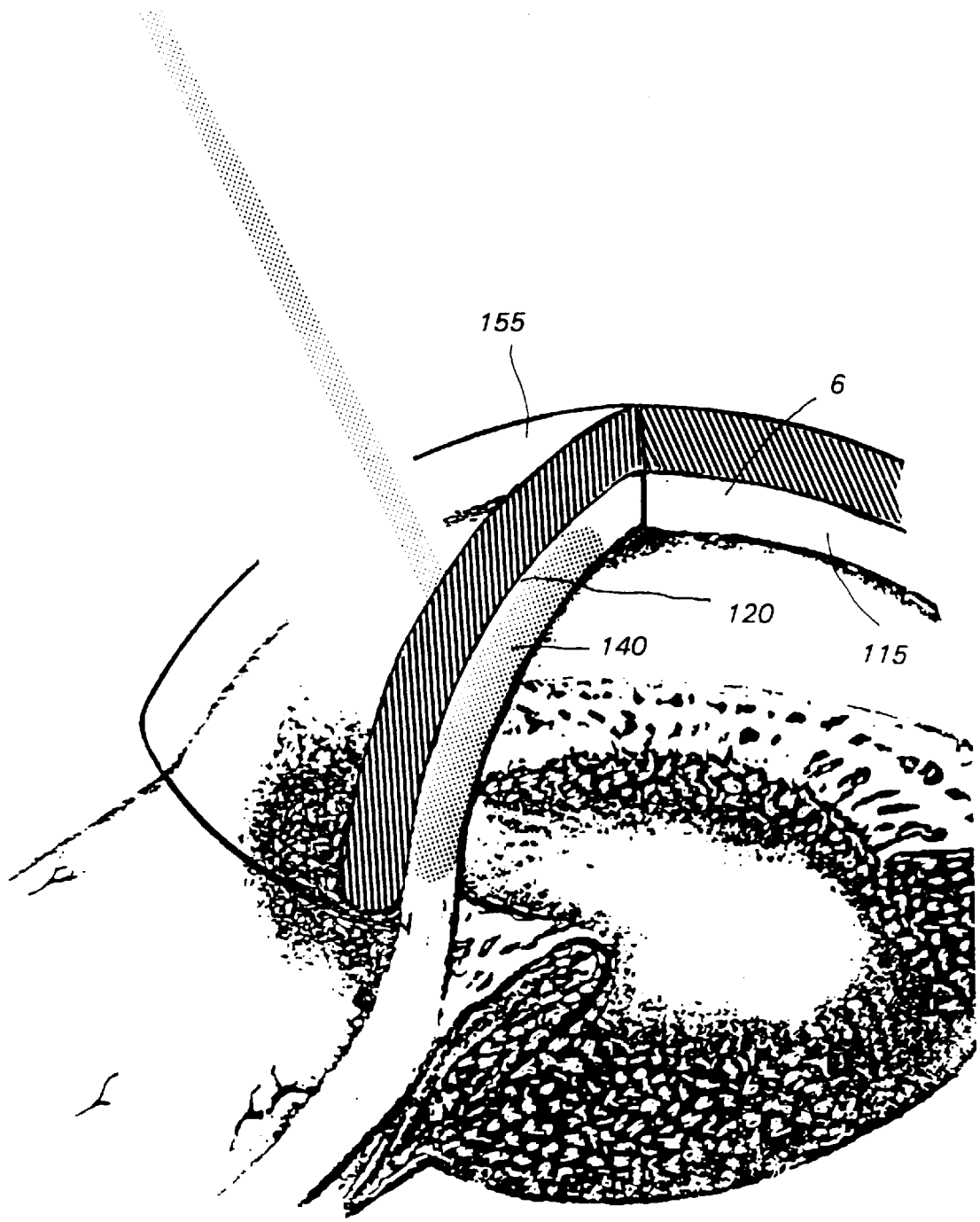
FIG. 12 depicts a schematic view of utilizing a contact lens device of an alternative method of the invention, the method similar to that of FIGS. 10A–10G but utilizing the contact lens as a heat sink.

Other operational modes that may be preferred relate to a feedback-controlled modes based on signals from thermal sensor shown in FIG. 12. In a first feedback controlled mode, radiometric surface temperature at the anterior corneal surface 100 may be monitored with sensor 150, e.g., a 1 mm.$^2$ liquid $N_2$ cooled HgCdTe infrared (IR) detector with a focal plane from about 10 mm. to 200 mm. from anterior surface 100 of cornea 6. The IR detector element may be optically filtered as is known in the art with an appropriate bandpass filter. The detection system further may be configured with collection optics to allow the detector to detect peak surface temperatures in any treatment zone 77a–77d simultaneously. Alternatively, there may be a plurality of such IR detectors with an individual detector for each zone 77a–77d, or on detector covering two zones etc. Such a IR detector may be a Model MDD-10-EO-S1 from Cincinnati Electronics, Inc., Mason, Ohio. In the simplest feed-back controlled mode, the dosimetry control system 85 may simply terminate photonic energy delivery upon detected surface temperature reaching a pre-set, for example any temperature between 42° C. and 58° C. The detected temperature of anterior surface 100 of the cornea is predictive of temperatures within stroma 115 by means of biological thermal modeling.

In another feedback controlled operational mode, the dosimetry control system 85, which typically includes microprocessor 140 together with an appropriate software program, can be designed to modulate power levels of the photonic energy source at any level among a continuous range of power levels as the emitters 50A–50D scan a zone 77a–77d. For example, each zone may have an IR detector that is adapted to modulate power in that zone with the objective of maintaining a particular surface temperature or turning the power off at a high limit and turning power on again at a low limit temperature.

The software that is part of the dosimetry control system, as the term is used herein, includes a conventional software program, a program within a programmable chip, or any other form of algorithm carried in any form of memory storage system. Within the hardware portion of dosimetry control system 85, there may be a keyboard, disk drive or other non-volatile memory system, displays as are well known in the art for operating such a system (see FIGS. 9 and 14).

The feedback control component of the dosimetry control system described above is based on signals from an IR detector. It should be appreciated that the feedback control or modulation of photonic energy delivery may be based on several other optical detection modalities that may be utilized to insure that excess energy is not delivered to prevent (i) corneal epithelial desiccation or ablation, (ii) stromal denaturation or shrinkage, or (iii) other undesirable stromal characterizations. It should be appreciated that such alternative detection systems are within the scope of the present invention and include: polarization-sensitive optical coherence tomographic (PS-OCT) signaling to insure that birefringence alternations do not occur in stromal tissue which may be a precursor to tissue denaturation; diffusing-wave spectroscopic methods of tissue characterization; two-photon fluorescence imaging; time-gated imaging using snake-like photons; general OCT methods; or measurements of back-scattered light.

In another embodiment of LMSR device, it should be appreciated that all of the above-described methods could additionally utilize a contact lens 155 as a heat sink as shown in FIG. 12. The contact lens 155 could be made of any material such as sapphire, quartz of plastic as is known in the art. The effect of such a heat sink contact lens would be to cool the anterior surface 100 of cornea 6 during the LMSR treatment which would maintain epithelium 120 at a lower temperature than otherwise might be the case. More preferably, the contact lens 155 could be cooled by any suitable means, either prior to treatment or during the LMSR treatment, to further maintain the epithelium at a lower temperature than would otherwise be possible. Also, as will be described in a subsequent disclosure, the thermal sensor 150 could provided with feedback circuitry to modulate power to the photonic energy source based on the cooled temperature of the heat-sink contact lens 155.

Figure 13:
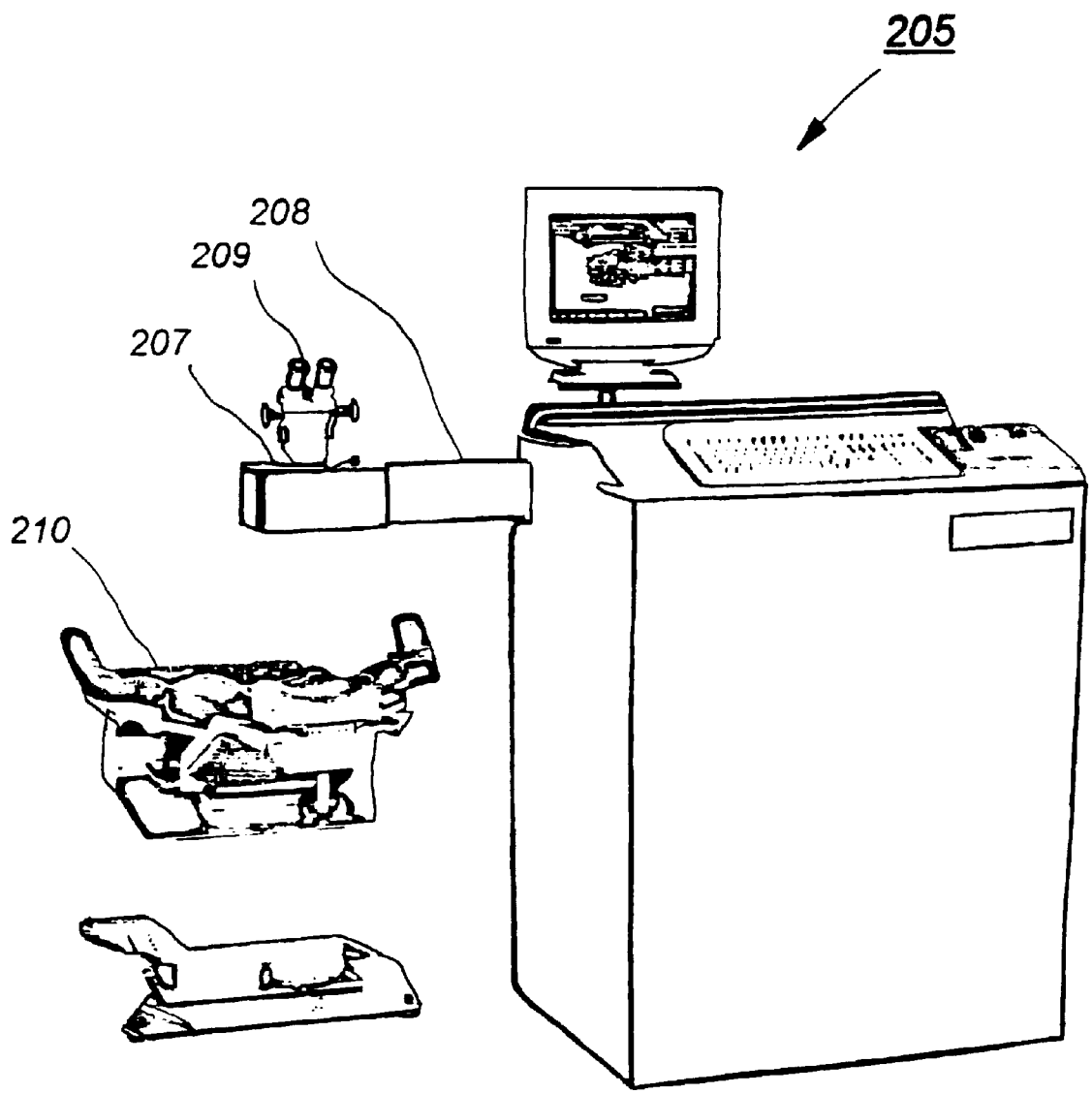
FIG. 13 is a perspective view of another embodiment of the present invention utilizing a device similar to that of FIGS. 5 though 9 integrated into a laser therapeutic treatment system (e.g., LASIK or PRK), the combination of which operates along or about the visual axis of the patient.
Figure 14:
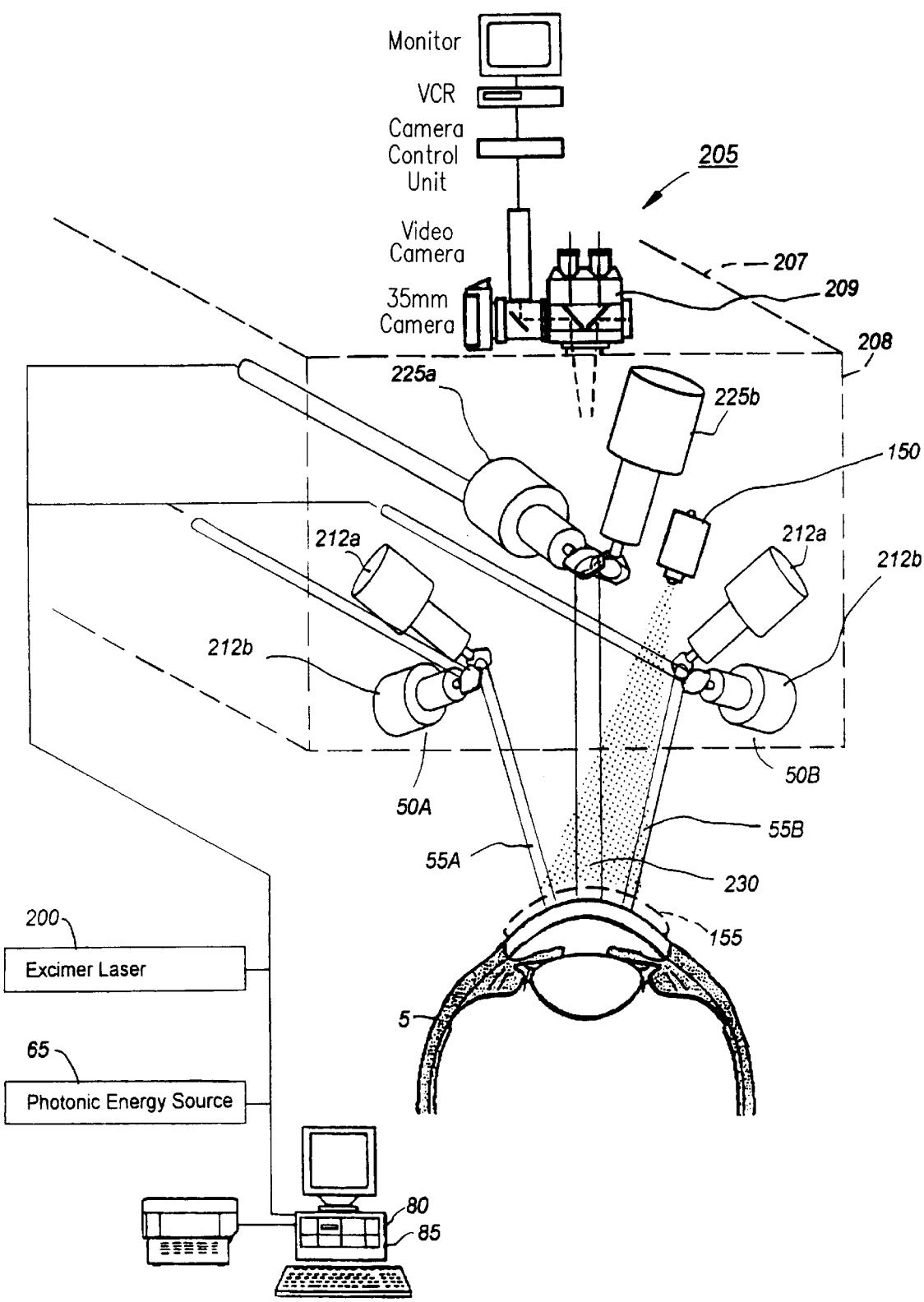
FIG. 14 is a schematic view of the working end of the combined embodiment of FIG. 14 taken along line 14—14 of FIG. 13.

FIG. 14 illustrates an alternative embodiment of the last-described LMSR device integrated with an adjunct therapeutic device 200 into a combined LMSR/LASIK-PRK system 205 with the adjunct device operating along optical axis 15 of the device and the patient's eye. The combined system 205 is shown in FIGS. 13–14 with working end 207 of arm 208 and biomicroscope 209 extending over chair 210 in which the patient is in a reclining position. FIG. 14 is an enlarged schematic view of working end 207 showing two emitters 50A and 50B with scanners 70A and 70B. Each galvanometric scanner has an x-galvo 212a and a y-galvo 212b to deliver beams 55A and 55B to the patient's cornea with intermediate flat-field (or other) lenses indicated at 215. Heat sink 155 is shown over eye 5 which would be removed before the LASIK/PRK procedure. The thermal sensor is indicated at 150. The LASIK/PRK is a scanning laser system 200 with a wavelength in the range of $\lambda$=193 to 230 nm, such as an excimer-type laser that adapted for corneal resurfacing is conjunction with x-galvo 225a and y-galvo 225b directing beam 230 through lens 232. A monitor, video camera, still camera, camera control unit and VCR may be made a part of the system. Typically aiming beams 88 (collectively) are directed by mirrors 233 (collectively). In another similar embodiment (not shown), the LMSR device can be integrated directly into a corneal topographic device.

4. Semiconductor Contact Lens Device for Thermoelectric Cooling of the Cornea. As described above in this specification regarding the method illustrated in FIG. 12, a heat sink contact lens may be used to cool the anterior surface of the cornea and to prevent dehydration of the anterior cornea during the above-described method of thermal relaxation of stresses in the cornea.

Figure 15:
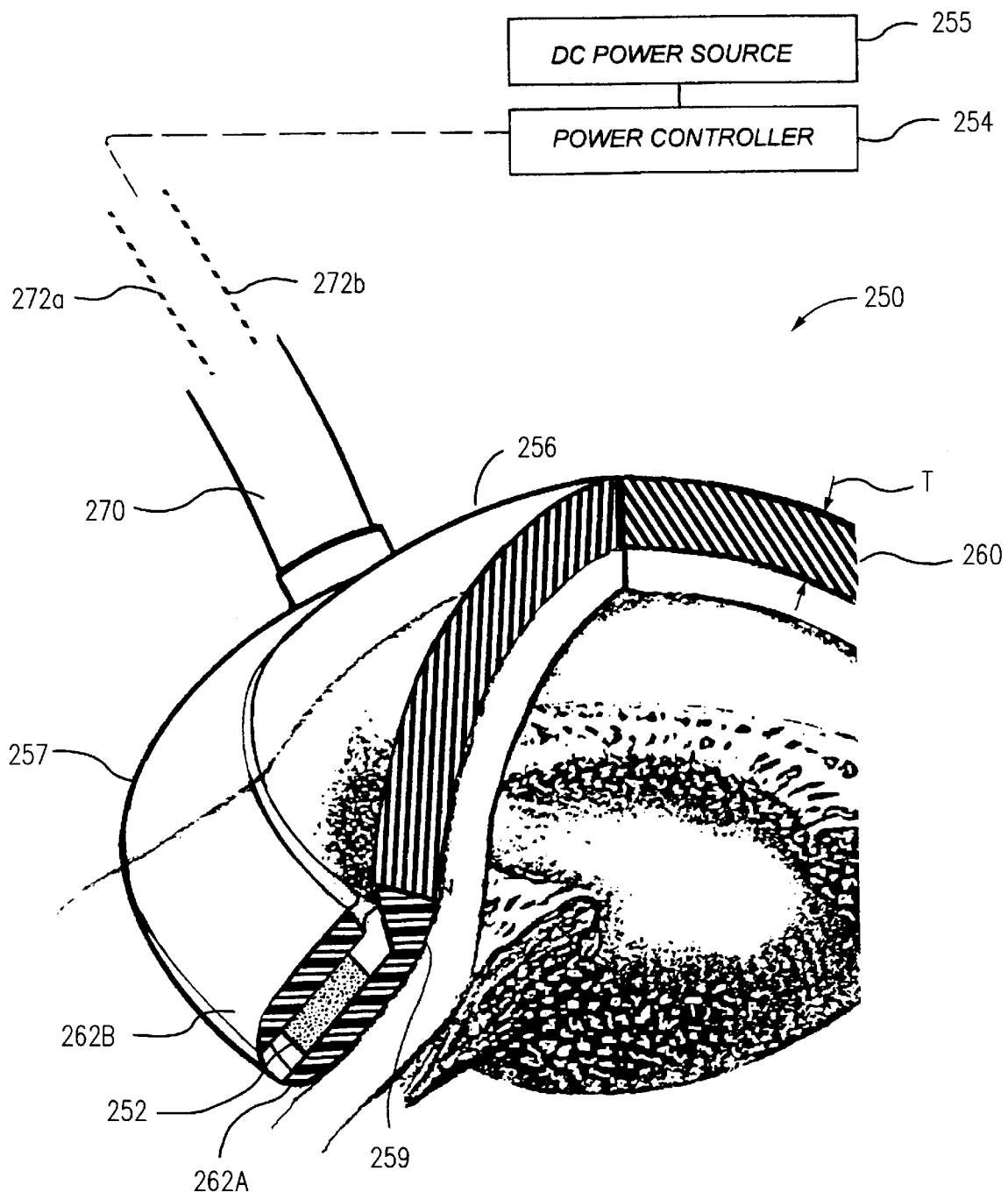
FIG. 15 depicts a partial sectional view of the dynamic semiconductor cooling contact lens of the present invention together with a block diagram of a power source and power controller.

Referring now to FIG. 15, an alternative novel embodiment of contact lens heat sink is shown, which can be described as an "active" or "dynamic" form of heat sink lens device 250 that utilizes a series of semiconductor (Peltier) paired elements 252 (made up of individual conductive block elements 253a and 253b) operatively connected to a direct current power controller 254 and direct current source 255 which is adapted to (i) pre-cool the cornea before an LMSR treatment, (ii) to cool the cornea rapidly following a LMSR treatment, or (iii) to dynamically cool the anterior surface of the cornea during an LMSR procedure based on temperature feedback from temperature sensors in the lens 250 to more precisely control the optothermal effects developed by the LMSR irradiation. (As described below, the dynamic cooling lens 250 may be used in any photothermal treatment of the cornea or sclera).

Figure 16:
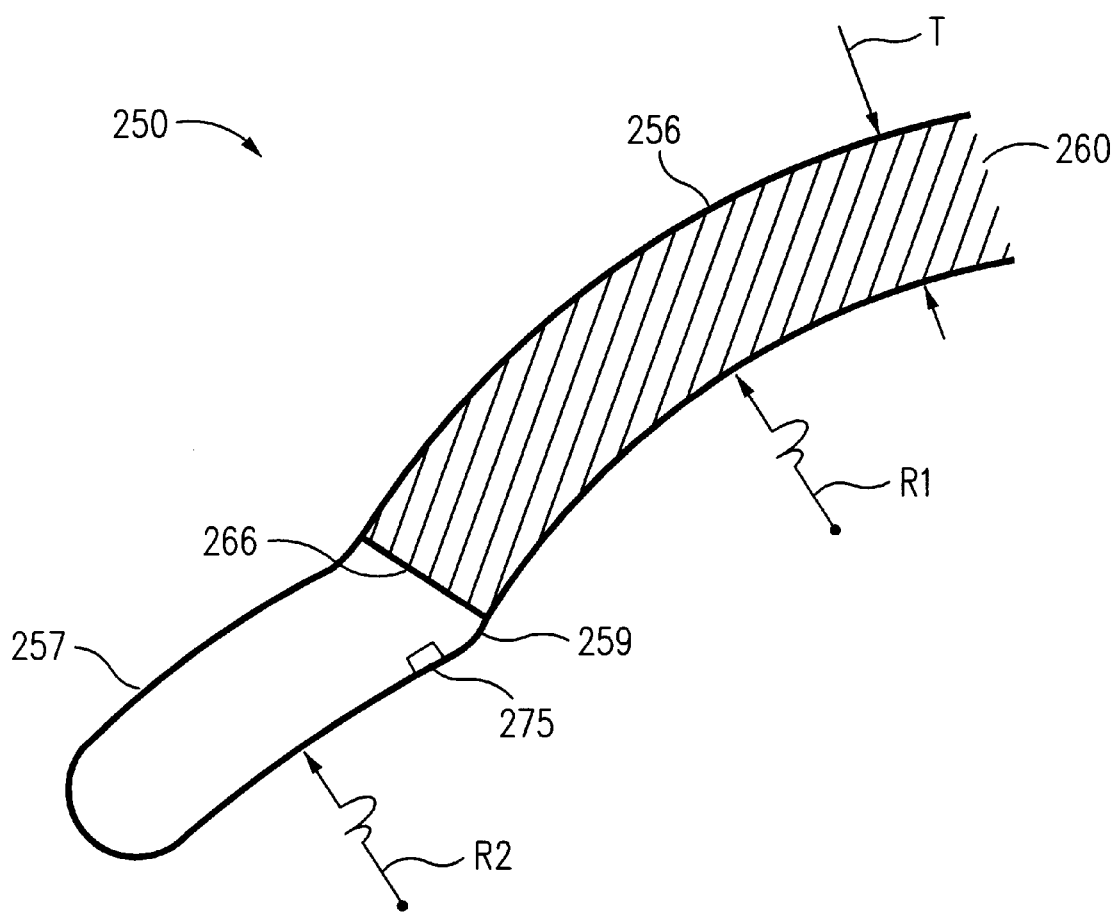
FIG. 16 depicts a sectional view of the semiconductor cooling contact lens of FIG. 15 with radius dimensions of sphero-concave portions.

As shown in FIG. 16, a sectional view of dynamic cooling lens 250 indicates a medial portion 256 that is sphero-concave with a first radius R1 ranging between about 6.0 mm. and 8.5 mm. which corresponds to the radius of curvature of a human cornea. The perimeter portion 257 of the lens is also sphero-concave and has a second radius R2 ranging between about 8.0 mm. and 13.0 mm. which corresponds to the radius of curvature of a sclera. In general, the semiconductor paired elements 252 are carried in the perimeter portion 257 and at most partly in an outer section 259 of medial portion 256 of lens 250 for the reason that most of the medial portion 256 of the lens must be of transparent material to allow the transmission of light beams therethrough. The transparent portion of the contact lens is indicated at 260 and preferably is of a transparent material with a high thermal conductivity and may be plastic, quartz, sapphire or another similar material.

Figure 17:
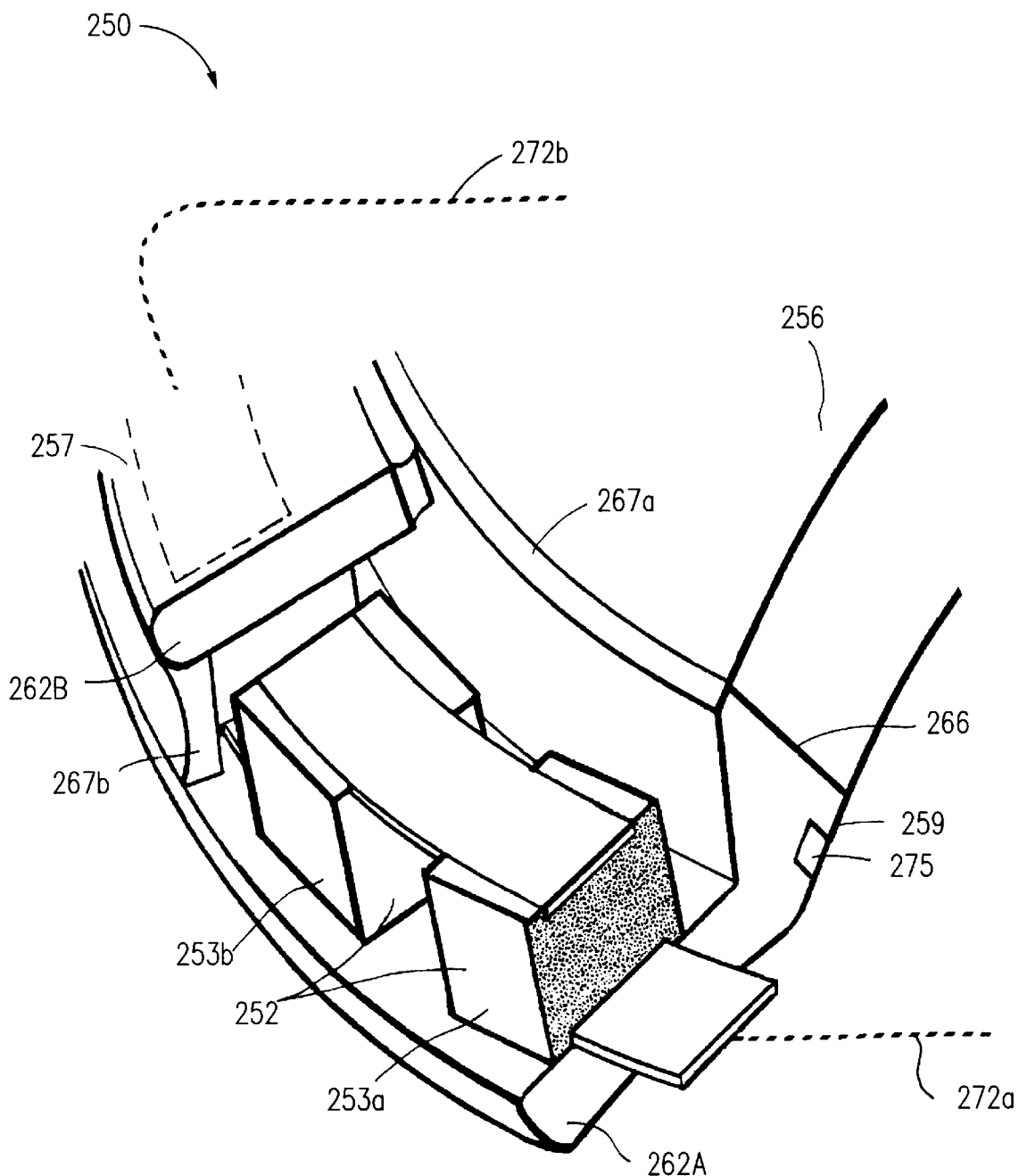
FIG. 17 is an enlarged cut-away view of a portion of the semiconductor cooling elements of the contact lens of FIG. 15.

Referring now to FIGS. 15 & 17, the semiconductor block elements 253a and 253b are bisimuth telluride or another similar material as are known in the art. When current passes through the junction of two different types of conductive block elements, it results in a temperature change (called a Peltier effect). Bismuth telluride is a good conductor of electricity but a poor conductor of heat. The semiconductor cooling mechanism thus consists of a number of p-type block elements indicated at 253a and n-type block elements 253b carried as pairs or couples that are connected electrically in series and carried between first (inner) surface element 265A and second (outer) surface element 265B of perimeter portion 257 of lens 250. The bismuth telluride block elements 253a and 253b are heavily doped to create an excess (n-type) of electrons (element 253a) or a deficiency (p-type) of electrons (element 253b) with conductor material 263 connecting the block elements as shown in FIG. 17. The semiconductor paired elements 252 are bonded to the thermally conductive first (inner) surface element 265A and second (outer) thermally conductive surface element 265B, which surface elements may be any suitable material such as a ceramic. The thermally conductive first (inner) surface 265A further is heat-conductively bonded along edge 266 to the medial transparent portion 256 to conduct heat from the medial portion to first surface 265A. As can be seen further in FIG. 17, insulator elements at 267a and 267b are provided to isolate the heat-rejecting second (outer) surface element 265B from the other parts of lens 250, but it should be appreciated that an air gap may be provided instead of an insulator material. When the lens device 250 is connected via cable 270 to a direct current power source (FIG. 15), the current flow causes heat to move from first (inner) surface element 265A to outer second (outer) surface element 265B where the heat is rejected or dissipated into the atmosphere. As can be seen in FIG. 15, cable 270 has current-carrying conductive wires 272a and 272b which are connected to direct current source 255. The engineering of such a semiconductor cooling system for integration into a dynamic cooling lens may be provided by a specialty engineering firm, e.g., Melcor Corporation, 1040 Spruce Street, Trenton, N.J. 08648. The thickness T of lens 250 may be any suitable dimension in the medial transparent portion 256 and the thickness of perimeter portion 257 may be similar or greater to accommodate the semiconductor elements 252 (FIG. 17).

As shown in FIGS. 16 & 17, one or more temperature sensors 275 such as thermocouples or thermisters are provided in medial portion 256 or the cooling side of perimeter portion 257 which are operatively connected via a wire (not shown) in cable 270 to provide signals to direct current controller 254. The power controller 254 includes algorithms or software 280 and circuitry that will modulate of terminate power from direct current source 255 to provide greater or lesser cooling of the corneal surface by lens 250 during or after the LMSR treatment.

In use, the lens 250 may be placed upon the patient's eye after an initial corneal topography diagnosis is completed as described above. One important advantage of the cooling lens 250 is that it will maintain corneal (and particularly corneal epithelial layer) hydration at a particular level or within a particular range during an LMSR treatment. (It should be appreciated that a cooling lens 250 may be useful to dynamically control changes in corneal temperature, hydration, anisotropy and absorption coefficients for any other optothermal treatment of the cornea, such as (i) elevation of corneal temperature for biostimulation purposes; (ii) elevation of corneal temperature in a photocoagulation, photodenaturation modality or so-called tissue photoshrinkage modality to alter corneal refractive power; (iii) or in any photothermal energy delivery to effect the morphology of the trabecular meshwork in a glaucoma treatment (see co-pending U.S. patent application Ser. No. 09/102,533 (Atty. Docket No. S-DESC-003) filed Jun. 22, 1998 titled "Devices and Techniques for Light-Mediated Stimulation of Trabecular Meshwork in Glaucoma Therapy" incorporated herein by reference. In glaucoma therapy, the semiconductor blocks may be moved the center of the lens with the perimeter transparent). It should be further appreciated that cooling lens 250 may be used to control corneal temperature, hydration, anisotropy and absorption coefficients for any other non-optothermal corneal treatments, for example, photo-acoustic treatments or other non-thermal photodisruption treatments to cut corneal tissue, such as femto-second or pico-second laser photodisruptive cutting (i.e., for cutting corneal flaps) which may cause transient temperature effects, and in which hydration control and absorption control may be important.

Figure 18:
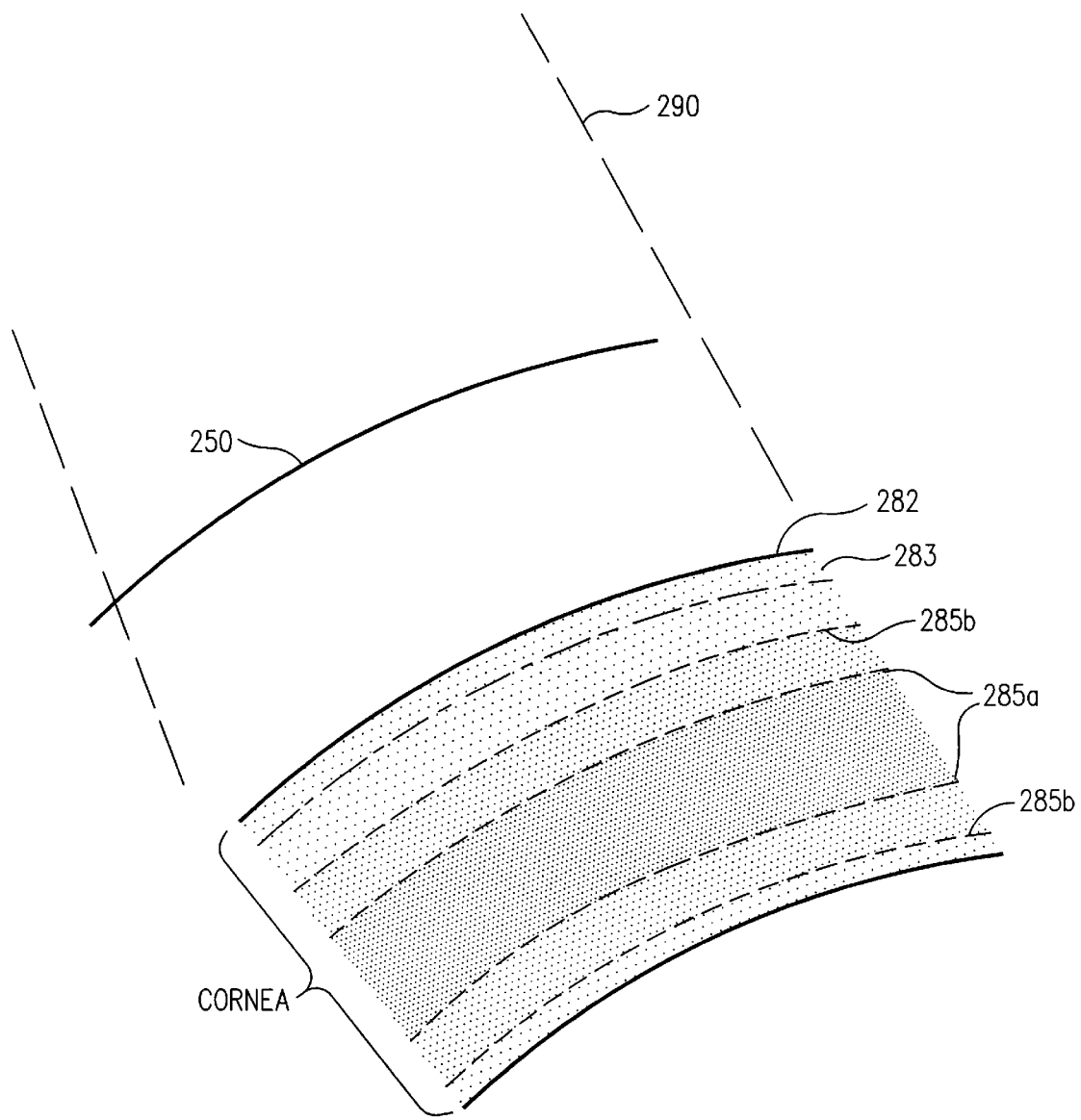
FIG. 18 is a sectional view of a medial portion of the semiconductor cooling contact lens of FIG. 15 in contact with corneal tissue depicting a method of the present invention in cooling surface layers while contemporaneously elevating the temperature of subsurface layers.

As can be seen in FIG. 18, during any photothermal treatment, the dynamic cooling lens 250 may be used to create a thermal gradient wherein the anterior surface 282 and epithelial layer 283 of the cornea is cooler than a mid-stromal portion 284 of the cornea. Such a thermal gradient is indicated by exemplary isotherms 285a and 285b and may be accomplished easily by dynamically cooling the anterior layers as a light energy beam 290 is pulsed intermittently at any suitable sequence ranging from about 10 ns. to 100 ms. pulse durations with 10 ns. to 1.0 second pulse repetition rates that allow heat to removed from the anterior surface of the cornea while temperature builds up in the mid-stromal regions due to the thermal relaxation time of tissue in the mid-stroma. By this means, the lens device 250 may reduce or prevent excessive epithelial cell death to moderate any wound healing response in the epithelium while still developing the increased temperature levels in less anterior portions of the cornea for a LMSR treatment or any of the other above-mentioned photothermal treatments of a patient's cornea.

In another method of the invention, it should be appreciated that a dynamic cooling lens 250 may combined with direct current power controller 254 in which current flow is reversed thereby causing a reverse of the above-described Peltier effect to deliver heat to the anterior surface of the cornea. For example, the LMSR treatment may be enhanced by a pre-heating of the cornea with the lens 250 to a certain temperature to alter anisotropy or absorption coefficients before utilizing light energy to elevate corneal temperature to relieve stress. Thereafter, the controller 254 may be utilized as described above to dynamically cool the cornea.

In yet another similar device and method of the present invention, a cooling lens member or cooling surface-contacting member may be formed in any flat or other suitable shape to fit in contact with any tissue surface. The Peltier elements may be carried in any manner about a perimeter or interior of a transparent thermally conductive member. A similar method thus may be used to elevate the temperature of subsurface tissue layers while cooling surface tissue layers in a wide range of thermotherapies. The method generally would include positioning a transparent portion of the surface-contacting member in contact with a surface layer of an anatomic tissue (cf. FIG. 18), actuating a direct current source operatively connected to the Peltier elements thereby conductively cooling said anatomic tissue either before, contemporanous with, or after the energy delivery step, such energy delivery step including providing and directing a photonic energy beam at an intensity, duration and repitition rate through said transparent portion of said surface-contacting member to elevate the temperature of the anatomic tissue. Thus, the energy of the photonic beam will be absorbed in the anatomic tissue and will elevate the temperature of underlying tissue layers more greatly than the surface layer since the surface is conductively cooled by the surface-contacting member. Further, it should be appreciated that such a cooling surface-contacting member may be adapted to fit against tissue (e.g., the epidermis) or a cooling surface-contacting member may be one or both sides of jaw-type structure that is adapted to capture the tissue layers that are targeted for treatment. The optothermal therapies desired to be performed on the subsurface tissue layers and that are the subject of the method of the invention may include bio-stimualtion of tissue, photocoagulation of tissue, photodenaturation or so-called photoshrinkage of tissue, photodisruption of tissue or fusion, welding, or bonding of tissue or any other photothermal therapy or photodynamic therapy wherein it is desirable to cool surface tissue while elevating underlying tissue layers.

Specific features of the invention are shown in some drawings and not in others, and this is for convenience only and any feature may be combined with another in accordance with the invention. Further variations will be apparent to one skilled in the art in light of this disclosure and are intended to fall within the scope of the appended claims.

What is claimed is:

1. A system for cooling an anterior portion of a patient's cornea to facilitate a photothermal treatment of a less anterior of the patient's cornea for altering corneal morphology, comprising:

a sphero-concave contact lens member having a first inner surface and a second outer surface, the lens member formed to contact an anterior surface of a patient's eye;

a central portion of said lens member of thermally conductive material that is transparent;

a perimeter portion of said lens member carrying a plurality of paired p-type and n-type semiconductor blocks comprising Peltier elements within inner and outer surfaces of said perimeter portion;

a direct current source operatively connected to said plurality of paired p-type and n-type semiconductor blocks.

2. A method of cooling an anterior portion of a patient's cornea to facilitate a photothermal treatment of a less anterior of the patient's cornea for altering corneal morphology, comprising the steps of:

providing a sphero-concave contact lens member of thermally conductive material having a medial transparent portion and a perimeter portion carrying at least one Peltier element;

positioning said medial portion of said lens member in contact with an anterior surface of the patient's cornea;

actuating a direct current source operatively connected to said at least one Peltier element thereby conductively cooling said cornea;

directing a photonic energy beam at an intensity, duration and repitition rate through said transparent lens portion about said anterior corneal surface;

wherein energy of said photonic beam is absorbed thus elevating the temperature of less anterior portions of the cornea while the lens element conductively cools said anterior surface of the cornea.

3. A method of cooling a surface layer of anatomic tissue to facilitate a thermal treatment of an underlying tissue layer for altering tissue morphology, comprising the steps of:

providing a surface-contacting member of thermally conductive material having a transparent portion coupled with an adjacent portion carrying at least one Peltier element;

positioning said transparent portion of said surface-contacting member in contact with said surface layer of anatomic tissue;

actuating a direct current source operatively connected to said at least one Peltier element thereby conductively cooling said anatomic tissue; and directing a photonic energy beam at an intensity, duration and repitition rate through said transparent portion of said surface-contacting member;

wherein energy of said photonic beam is absorbed in said anatomic tissue thus elevating the temperature of underlying tissue layers while the surface-contacting member conductively cools said surface layer.

* * * * *